United States Patent
Dala-Krishna

(10) Patent No.: US 8,317,711 B2
(45) Date of Patent: Nov. 27, 2012

(54) OSCILLATING PHASED-ARRAY ULTRASOUND IMAGING CATHETER SYSTEM

(75) Inventor: Praveen Dala-Krishna, Sicklerville, NJ (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 870 days.

(21) Appl. No.: 11/764,194

(22) Filed: Jun. 16, 2007

(65) Prior Publication Data
US 2008/0312536 A1 Dec. 18, 2008

(51) Int. Cl.
*A61B 1/00* (2006.01)
(52) U.S. Cl. .......................... 600/459; 600/437
(58) Field of Classification Search .................. 600/407, 600/437, 459, 462; 604/528; 73/627, 633
See application file for complete search history.

(56) References Cited

U.S. PATENT DOCUMENTS

| | | | |
|---|---|---|---|
| 4,161,121 A | 7/1979 | Zitelli et al. | |
| 4,241,610 A | 12/1980 | Anderson | |
| 4,462,408 A | 7/1984 | Silverstein et al. | |
| 4,519,260 A | 5/1985 | Fu et al. | |
| 4,576,177 A | 3/1986 | Webster, Jr. | |
| 4,605,009 A | 8/1986 | Pourcelot et al. | |
| 4,841,977 A | 6/1989 | Griffith et al. | |
| 4,869,258 A * | 9/1989 | Hetz | 600/446 |
| 4,890,268 A | 12/1989 | Smith et al. | |
| 4,917,097 A | 4/1990 | Proudian et al. | |
| 4,951,677 A | 8/1990 | Crowley et al. | |
| 5,002,059 A | 3/1991 | Crowley et al. | |
| 5,090,956 A | 2/1992 | McCoy | |
| 5,105,819 A | 4/1992 | Wollschlager et al. | |
| 5,152,294 A | 10/1992 | Mochizuki et al. | |
| 5,158,087 A | 10/1992 | Gatzke | |
| 5,170,793 A | 12/1992 | Takano et al. | |
| 5,195,968 A | 3/1993 | Lundquist et al. | |
| 5,254,088 A | 10/1993 | Lundquist et al. | |
| 5,279,559 A | 1/1994 | Barr | |
| 5,307,816 A | 5/1994 | Hashimoto et al. | |
| 5,309,914 A | 5/1994 | Iinuma | |
| 5,325,860 A | 7/1994 | Seward et al. | |
| 5,335,663 A * | 8/1994 | Oakley et al. | 600/463 |
| 5,336,182 A | 8/1994 | Lundquist et al. | |
| 5,345,938 A | 9/1994 | Nishiki et al. | |

(Continued)

OTHER PUBLICATIONS

U.S. Appl. No. 11/610,357, filed Dec. 13, 2006, Praveen Dala-Krishna.

(Continued)

*Primary Examiner* — Tse Chen
*Assistant Examiner* — Rochelle Reardon

(57) ABSTRACT

A dynamic ultrasound image catheter includes a catheter body with an acoustic window on the distal end, an ultrasound phased array transducer assembly configured to rotate within the acoustic window through an angle of rotation, an acoustic coupling fluid filling a gap between the transducer array and the acoustic window, and a drive motor at the proximal end of the catheter body that is configured to rotate the transducer array. The drive motor may transmit a rotational force to the ultrasound phased array transducer by a drive wire or by tension wires coupled to drive spools. A system processor coupled to the drive motor controls rotation of the transducer array and estimates the angular orientation of the transducer array. By taking ultrasound images at increments through the angle of rotation, the dynamic ultrasound image catheter can obtain images spanning a volume which can be processed to generate three-dimensional composite images.

30 Claims, 20 Drawing Sheets

U.S. PATENT DOCUMENTS

| | | | |
|---|---|---|---|
| 5,345,940 A | | 9/1994 | Seward et al. |
| 5,357,550 A | | 10/1994 | Asahina et al. |
| 5,358,478 A | | 10/1994 | Thompson et al. |
| 5,364,351 A | | 11/1994 | Heinzelman et al. |
| 5,372,138 A | | 12/1994 | Crowley et al. |
| 5,385,148 A | | 1/1995 | Lesh et al. |
| 5,395,327 A | | 3/1995 | Lundquist et al. |
| 5,438,997 A | | 8/1995 | Sieben et al. |
| 5,456,258 A | | 10/1995 | Kondo et al. |
| 5,456,664 A | | 10/1995 | Heinzelman et al. |
| 5,470,350 A | | 11/1995 | Buchholtz et al. |
| 5,488,955 A | * | 2/1996 | Dias .................... 600/459 |
| 5,499,630 A | | 3/1996 | Hiki et al. |
| 5,515,853 A | | 5/1996 | Smith et al. |
| 5,515,856 A | | 5/1996 | Olstad et al. |
| 5,531,686 A | | 7/1996 | Lundquist et al. |
| 5,560,362 A | | 10/1996 | Sliwa, Jr. et al. |
| 5,588,432 A | | 12/1996 | Crowley |
| 5,622,174 A | | 4/1997 | Yamazaki |
| 5,662,116 A | | 9/1997 | Kondo et al. |
| 5,697,965 A | | 12/1997 | Griffin, III |
| 5,699,805 A | | 12/1997 | Seward et al. |
| 5,701,897 A | | 12/1997 | Sano |
| 5,704,361 A | | 1/1998 | Seward et al. |
| 5,713,363 A | | 2/1998 | Seward et al. |
| 5,715,817 A | | 2/1998 | Stevens-Wright et al. |
| 5,715,825 A | * | 2/1998 | Crowley .................... 600/462 |
| 5,722,403 A | | 3/1998 | McGee et al. |
| 5,749,364 A | | 5/1998 | Sliwa, Jr. et al. |
| 5,788,636 A | | 8/1998 | Curley |
| 5,795,299 A | | 8/1998 | Eaton et al. |
| 5,797,848 A | | 8/1998 | Marian et al. |
| 5,800,356 A | | 9/1998 | Criton et al. |
| 5,807,324 A | | 9/1998 | Griffin, III |
| 5,846,205 A | | 12/1998 | Curley et al. |
| 5,888,577 A | | 3/1999 | Griffin, III et al. |
| 5,891,088 A | | 4/1999 | Thompson et al. |
| 5,906,579 A | | 5/1999 | Vander Salm et al. |
| 5,916,168 A | | 6/1999 | Pedersen et al. |
| 5,921,978 A | | 7/1999 | Thompson et al. |
| 5,928,276 A | | 7/1999 | Griffin, III et al. |
| 5,931,863 A | | 8/1999 | Griffin, III et al. |
| 5,935,102 A | | 8/1999 | Bowden et al. |
| 5,938,616 A | | 8/1999 | Eaton et al. |
| 5,954,654 A | | 9/1999 | Eaton et al. |
| 6,013,072 A | | 1/2000 | Winston et al. |
| 6,033,378 A | | 3/2000 | Lundquist et al. |
| 6,039,693 A | | 3/2000 | Seward et al. |
| 6,085,117 A | | 7/2000 | Griffin, III et al. |
| 6,144,870 A | | 11/2000 | Griffin, III |
| 6,171,248 B1 | | 1/2001 | Hossack et al. |
| 6,173,205 B1 | | 1/2001 | Griffin, III et al. |
| 6,190,353 B1 | | 2/2001 | Makower et al. |
| 6,210,333 B1 | | 4/2001 | Gardner et al. |
| 6,224,556 B1 | | 5/2001 | Schwartz et al. |
| 6,228,028 B1 | | 5/2001 | Klein et al. |
| 6,228,032 B1 | | 5/2001 | Eaton et al. |
| 6,261,246 B1 | | 7/2001 | Pantages et al. |
| 6,293,943 B1 | | 9/2001 | Panescu et al. |
| 6,306,096 B1 | | 10/2001 | Seward et al. |
| 6,306,097 B1 | | 10/2001 | Park et al. |
| 6,310,828 B1 | | 10/2001 | Mumm et al. |
| 6,360,027 B1 | | 3/2002 | Hossack et al. |
| 6,368,275 B1 | | 4/2002 | Sliwa et al. |
| 6,385,489 B1 | | 5/2002 | Griffin, III et al. |
| 6,398,731 B1 | | 6/2002 | Mumm et al. |
| 6,423,002 B1 | | 7/2002 | Hossack |
| 6,440,488 B2 | | 8/2002 | Griffin, III et al. |
| 6,443,894 B1 | | 9/2002 | Sumanaweera et al. |
| 6,475,148 B1 | | 11/2002 | Jackson et al. |
| 6,475,149 B1 | | 11/2002 | Sumanaweera |
| 6,482,161 B1 | | 11/2002 | Sumanaweera et al. |
| 6,485,455 B1 | | 11/2002 | Thompson et al. |
| 6,491,633 B1 | | 12/2002 | Krishnan et al. |
| 6,503,202 B1 | | 1/2003 | Hossack et al. |
| 6,517,488 B1 | | 2/2003 | Hossack |
| 6,527,717 B1 | | 3/2003 | Jackson et al. |
| 6,532,378 B2 | | 3/2003 | Saksena et al. |
| 6,554,770 B1 | | 4/2003 | Sumanaweera et al. |
| 6,589,182 B1 | | 7/2003 | Loftman et al. |
| 6,592,520 B1 | * | 7/2003 | Peszynski et al. ............ 600/459 |
| 6,605,043 B1 | | 8/2003 | Dreschel et al. |
| 6,607,488 B1 | | 8/2003 | Jackson et al. |
| 6,607,528 B1 | | 8/2003 | Quick et al. |
| 6,612,992 B1 | | 9/2003 | Hossack et al. |
| 6,645,147 B1 | | 11/2003 | Jackson et al. |
| 6,648,875 B2 | | 11/2003 | Simpson et al. |
| 6,709,396 B2 | | 3/2004 | Flesch et al. |
| 6,733,457 B2 | * | 5/2004 | Flesch et al. .................. 600/459 |
| 6,773,402 B2 | | 8/2004 | Govari et al. |
| 6,908,434 B1 | | 6/2005 | Jenkins et al. |
| 6,923,768 B2 | | 8/2005 | Camus et al. |
| 2003/0045796 A1 | | 3/2003 | Friedman |
| 2003/0158483 A1 | | 8/2003 | Jackson et al. |
| 2004/0082859 A1 | * | 4/2004 | Schaer .................... 600/459 |
| 2004/0097805 A1 | | 5/2004 | Verard et al. |
| 2004/0249282 A1 | | 12/2004 | Olstad |
| 2005/0080336 A1 | | 4/2005 | Byrd et al. |
| 2005/0203390 A1 | | 9/2005 | Torp et al. |
| 2005/0203410 A1 | * | 9/2005 | Jenkins .................... 600/459 |
| 2005/0228290 A1 | | 10/2005 | Borovsky et al. |
| 2006/0095025 A1 | * | 5/2006 | Levine et al. .................... 606/15 |
| 2006/0122514 A1 | | 6/2006 | Byrd et al. |
| 2007/0016060 A1 | * | 1/2007 | Hwang .................... 600/459 |
| 2008/0097403 A1 | * | 4/2008 | Donaldson et al. ........... 604/528 |

OTHER PUBLICATIONS

U.S. Appl. No. 11/610,386, filed Dec. 13, 2006, Praveen Dala-Krishna.

U.S. Appl. No. 11/772,161, filed Jun. 30, 2007, Praveen Dala-Krishna.

Crowley, R.J., et al., "Ultrasound Guided Therapeutic Catheters: Recent Developments and Clinical Results," Int'l Journal of Cardiac Imaging, 1991, pp. 145-156, Kluwer Academic Publishers, Netherlands.

Bom, N., et al., "Early and recent Intraluminal Ultrasound Devices," Int'l Journal of Cardiac Imaging, 1989, pp. 79-88, Kluwer Academic Publishers, Netherlands.

* cited by examiner

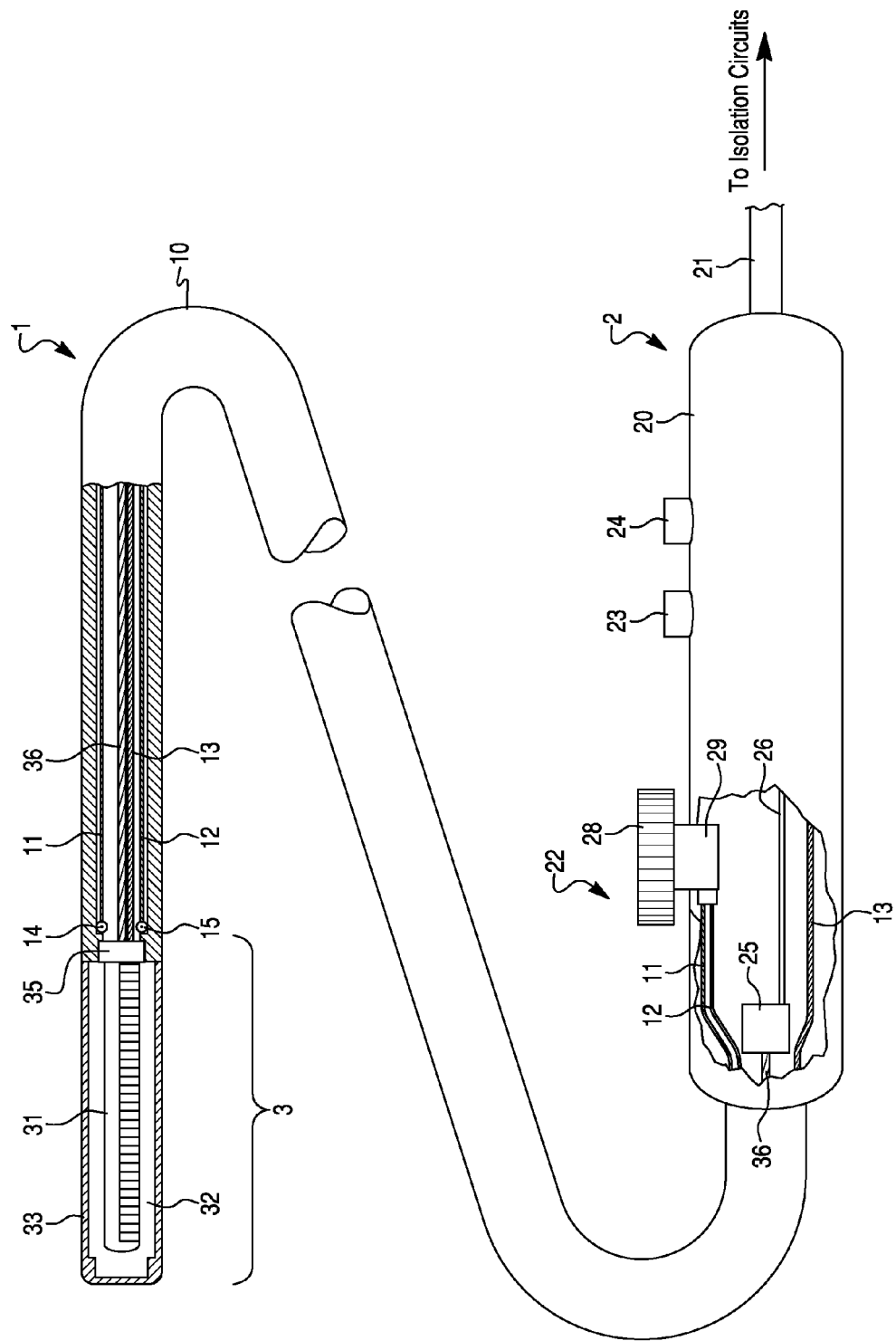

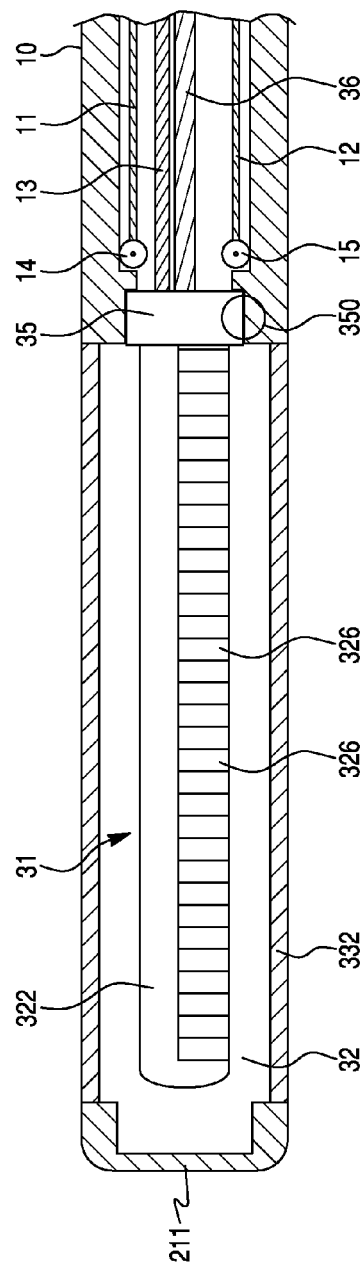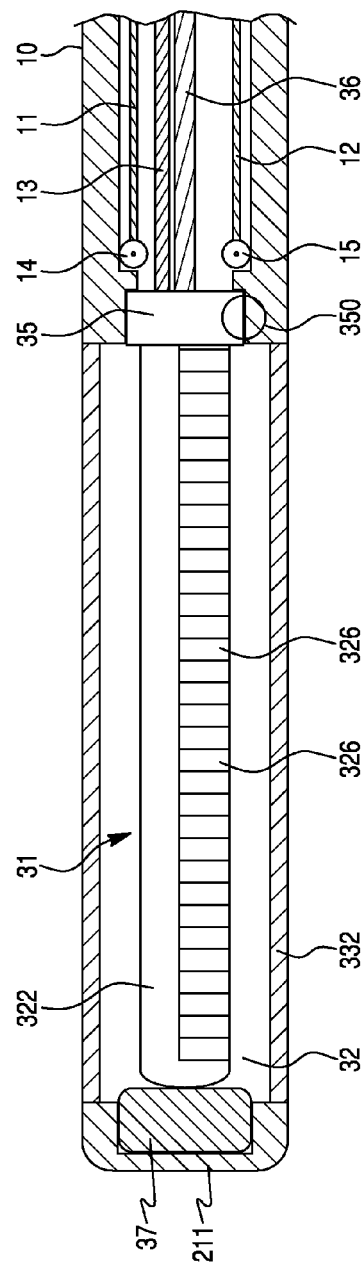

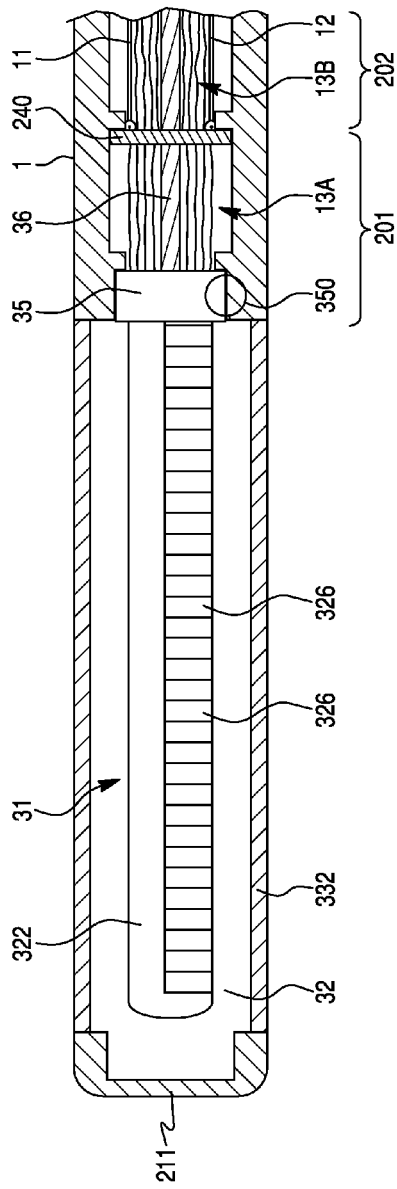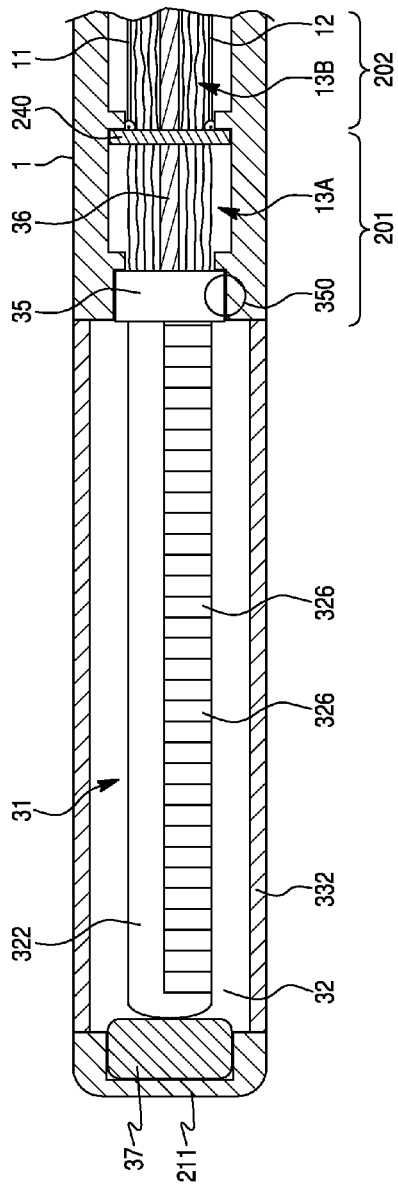

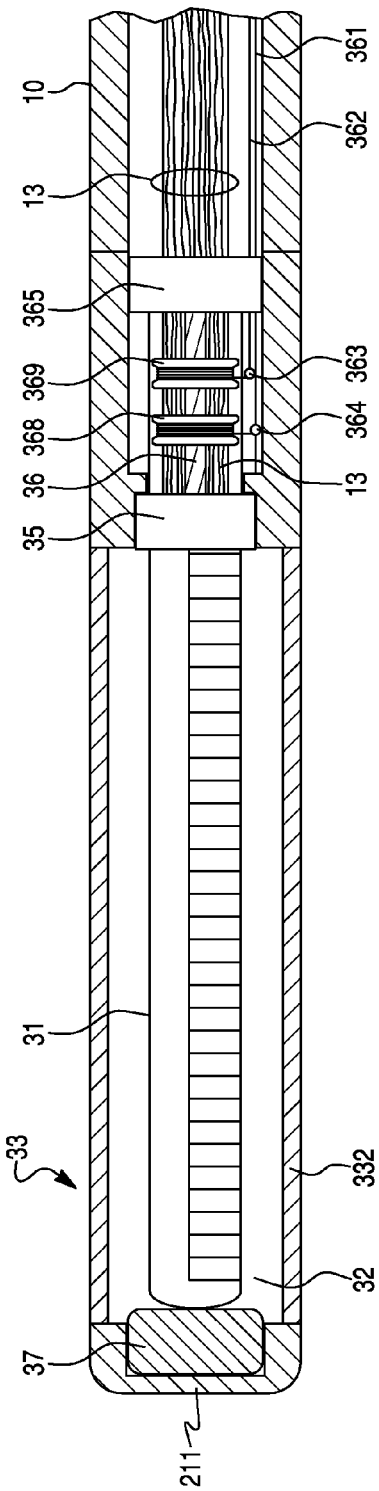
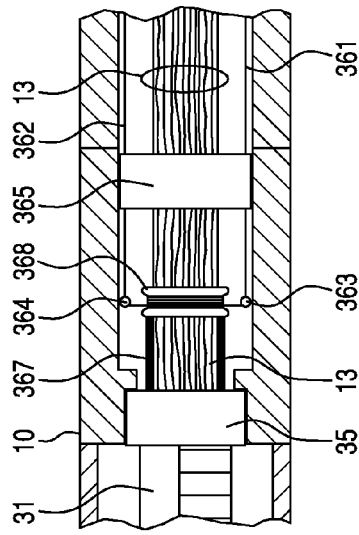
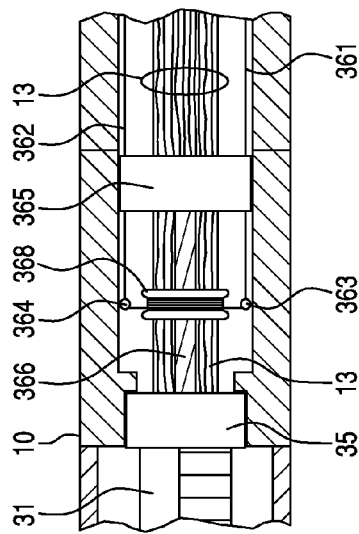

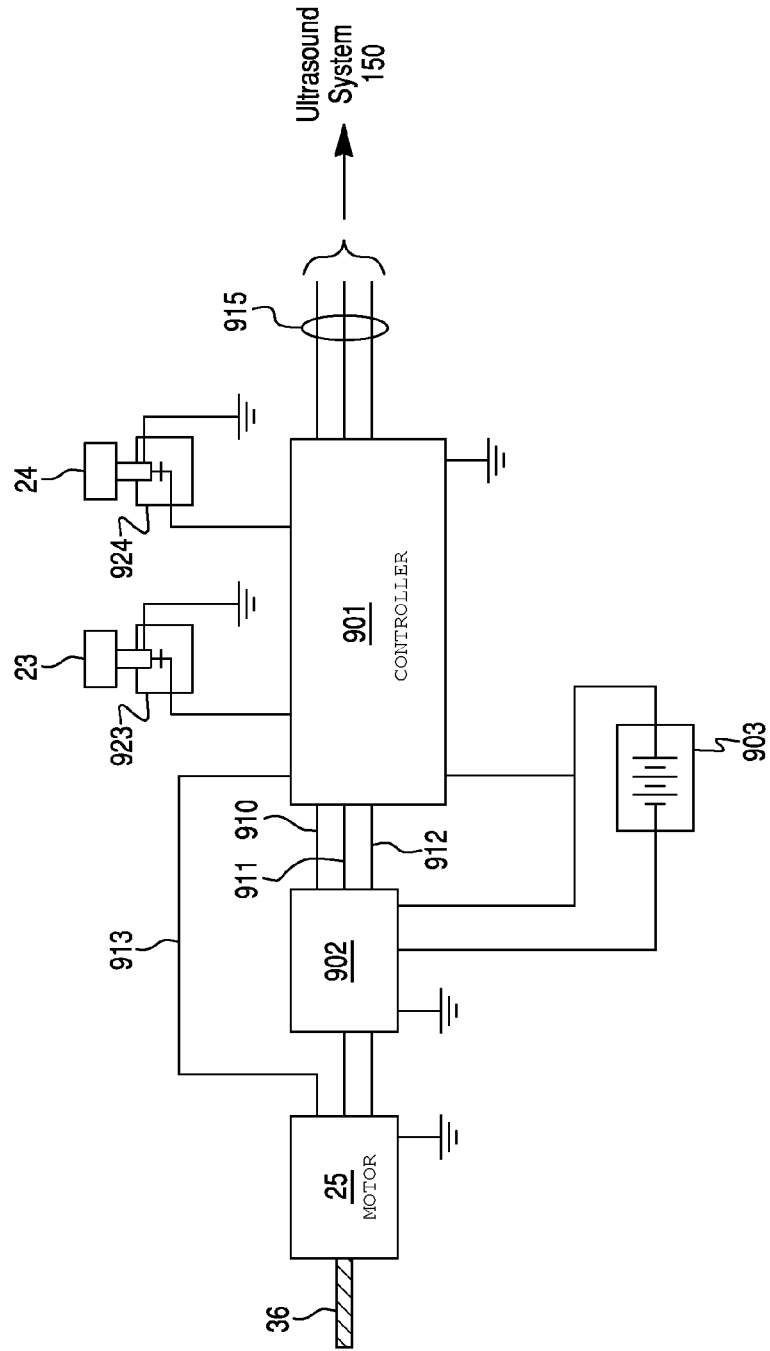

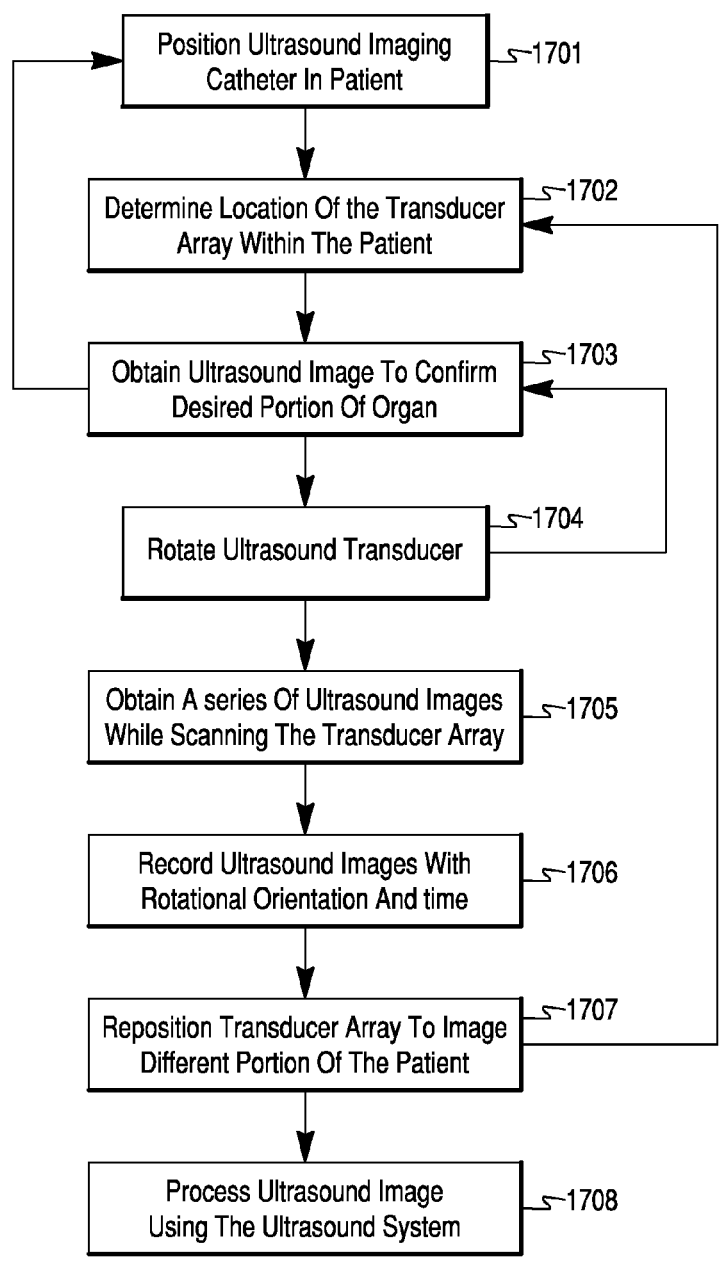

OSCILLATING PHASED-ARRAY ULTRASOUND IMAGING CATHETER SYSTEM

FIELD OF THE INVENTION

The present invention relates to medical diagnostic systems and methods, and more particularly to ultrasound imaging catheter systems with a rotating phased-array transducer.

BACKGROUND OF THE INVENTION

Recent advancements in miniaturization of ultrasound technology has enabled the commercialization of catheters including phased array ultrasound imaging transducers small enough to be positioned within a patient's body via intravenous cannulation. By imaging vessels and organs, including the heart, from the inside, such miniature ultrasound transducers have enabled physicians to obtain diagnostic images available by no other means.

The diameter of catheters, particularly intracardiac catheters, are necessarily restricted to about 10 French or smaller by the diameter and profile of blood vessels through which the catheter may be advanced. Consequently, catheter-born ultrasound transducers have been restricted to single transducer elements (providing only distance information) and linear phased-array transducer assemblies which provide a two-dimensional image.

SUMMARY OF THE INVENTION

The present invention is directed toward providing compact, portable ultrasound systems which can generate images suitable for rendering three-dimensional images of organs— particularly in connection with intra-body, percutaneous ultrasound probes, such as catheters and endoscopes containing ultrasound transducer arrays.

The embodiments of the present invention describe an imaging catheter which includes a stepper motor to allow the physician to generate an azimuthally rotation of the imaging elements about the catheter axis while producing a 3D image of the adjacent tissue.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain features of the invention.

FIG. 3 is a cross sectional view of an embodiment of a dynamic ultrasound imaging catheter.

FIGS. 4A and 4B are longitudinal cross sectional views of two embodiments of the distal end of the ultrasound imaging catheter shown in FIG. 3.

FIGS. 6A and 6B are cross sectional view of two alternative embodiments of the distal end of the dynamic ultrasound imaging catheter.

FIGS. 10A-10E are cross sectional views of alternative embodiments of the distal end of the dynamic ultrasound imaging catheter.

FIG. 13 is circuit block diagram of an embodiment of power and control circuits for the embodiment illustrated in FIG. 3.

FIG. 17 is a flow diagram of a method of using an embodiment of the dynamic ultrasound imaging catheter.

DETAILED DESCRIPTION OF THE PREFERRED EMBODIMENTS

Various embodiments of the present invention will be described in detail with reference to the accompanying drawings. Wherever possible, the same reference numbers will be used throughout the drawings to refer to the same or like parts.

As used herein, the terms "about" or "approximately" for any numerical values or ranges indicate suitable dimensional tolerances that allow the part or collection of components to function for their intended purposes as described herein. Also, as used herein, the terms "patient", "host", and "subject" refer to any human or animal subject and are not intended to limit the systems or methods to human use. Further, embodiments of the invention will be described for use with an intracardiac ultrasound transducer array catheter; however, the embodiments may be applicable to any medical ultrasound transducer.

Phased array ultrasound imaging catheter systems, particularly intracardiac ultrasound imaging catheters, generate two dimensional sliced images of tissue within the field of view of the transducer array. The ultrasound imaging catheter is limited to a small diameter, such as 6 to 10 French, so that it can be inserted into most organs of the body via catheterization through a vein or artery, or through small incisions such as in an arthroscopic procedure. For example, an intracardiac ultrasound catheter can be introduced into the heart through the vena cava to image the atria and ventricles from just outside or within the heart itself. Such access of the imaging sensor provides image details and perspective that are available by no other imaging means.

Figure 1:
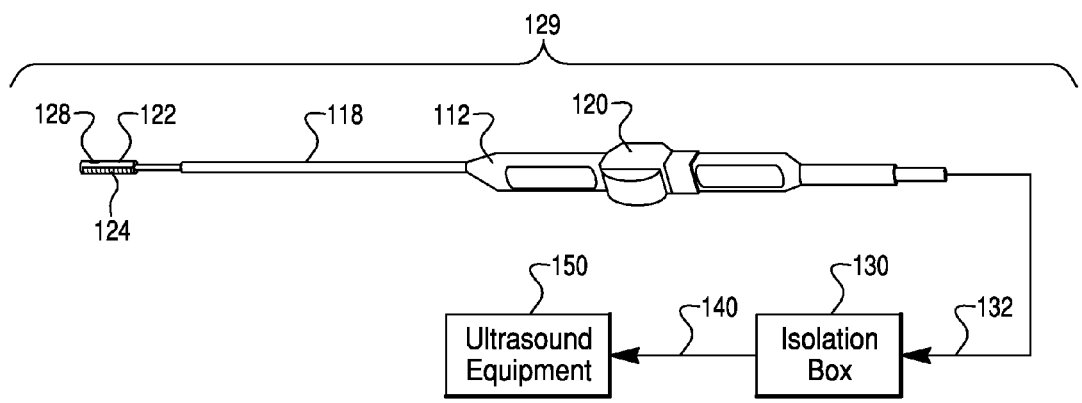
FIG. 1 is an illustration of a prior art intracardiac linear phased-array ultrasound imaging catheter.

A conventional ultrasound imaging catheter system is shown in FIG. 1. Such systems include an imaging probe 120 electrically coupled to an isolation box 130 which is coupled to an ultrasound equipment 150 via a cable 140. The imaging probe 120 includes a catheter 118 and transducer assembly 112 as shown in FIG. 1. The catheter assembly 112 includes an elongated catheter 118 generally in the form of a tube. The proximal end of the catheter 118 is connected to a handle mechanism 120 which can include mechanisms for controlling the steering of the ultrasound probe 122 mounted at the distal end of the catheter 118.

Figure 2:
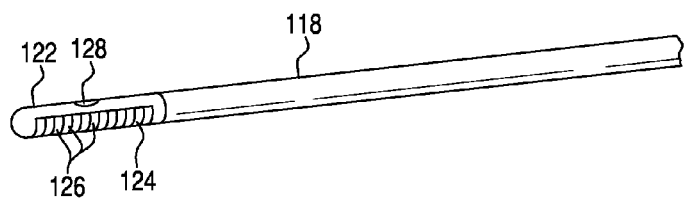
FIG. 2 is an illustration of a portion of the prior art ultrasound imaging catheter shown in FIG. 1.

The ultrasound probe 122, shown in more detail in FIG. 2, includes an ultrasound transducer assembly 124, which is comprised of a number of ultrasonic transducer elements 126 having wires connected thereto which are provided inside the catheter 118. Although only twelve or so transducer elements 126 are shown in FIG. 2, typical ultrasound transducer arrays include 64 transducer elements 126 and substantially any number of transducer elements may be employed as described in the prior application discussed above. Mounted near the distal end, such as on the reverse side of the ultrasound transducer probe 122 is a thermistor 128, which may be embedded within the probe 122. The thermistor 28 is positioned so as to be able to sense the temperature of the tissue in the vicinity of the probe 122 and/or the temperature of the probe 122 itself. Examples of phased array ultrasound imaging catheters used for intracardiac echocardiography and methods of using such devices in cardiac diagnosis are disclosed in the following U.S. Patent Application Publications—each of which is incorporated herein by reference in their entirety.

2004/0127798 to Dala-Krishna et al.;
2005/0228290 to Borovsky et al.; and
2005/0245822 to Dala-Krishna et al.

Commercially available ultrasound catheters are available from EP MedSystems, Inc. of West Berlin, N.J.

Electrical wires connected to the ultrasonic transducer elements 126 and the thermistor 128 pass through the inside of the catheter body 118 and are connected by a cable 132 to an isolation box 130 which passes the electrical signals to ultrasonic equipment 150 which operate in manners well known in the art.

The ultrasonic transducer elements 126 convert the electrical signals from the ultrasound equipment 150 into high frequency sound waves which propagate into a portion of a patient's anatomy, such as the heart. The same ultrasonic transducer elements 126 also receive ultrasound echoes reflected from anatomic structures and transform the received sound into electrical signals (e.g., by means of the piezoelectric effect). These electrical signals are conducted via cable 132 back to the isolation box 130 and then to the ultrasound equipment 150.

Within the ultrasound equipment 150, a signal generator generates electrical signals of ultrasonic frequencies which provided to the ultrasonic transducer elements 126. The signal generator produces signals of particular wave forms, frequencies and amplitudes as desired for imaging tissue. Beam former circuits within the ultrasound equipment 150 process signals sent to and received from the ultrasonic transducer elements 126 to enable phased-array ultrasound imaging. The beam former circuits may receive ultrasound signals from the signal generator and introduce phase lags for each ultrasonic transducer element 126 so that when the signals are applied to the transducer elements a narrow beam of sound emanates from the array due to constructive and destructive wave interactions as well known in the art of imaging ultrasound phased array transducers. Also, the beam former may receive signals from the transducer array and process the ultrasound echo signal data to calculate the amplitude and direction of the ultrasound echoes returned to the transducer elements 126 from each of many specific angles and distances. The beam former circuits may also determine the frequency or Doppler frequency shift of the signal returned form each of selected angles and distances from the transducer elements 126.

The isolation box 130 contains isolation circuitry which isolates unintended, potentially unsafe electrical currents and voltages from the catheter which contacts the patient. Examples of suitable isolation circuits are described in U.S. patent application Ser. No. 10/997,898 "Method And Apparatus For Isolating A Catheter Interface", published as U.S. Patent Publication No. 2005/0124898 to Borovsky et al filed on Nov. 29, 2004, the entire contents of which are hereby incorporated by reference. An example of such safety methods and systems is embodied in the ViewMate® catheter ultrasound system from EP MedSystems, Inc. of West Berlin, N.J.

The circuits and functionality of the isolation box 130 and ultrasound system 150 may be combined into a single unitary system as recently disclosed in U.S. patent application Ser. No. 11/610,778 entitled "Integrated Beam Former and Isolation For An Ultrasound Probe" and Ser. No. 11/610,866 entitled "External and Internal Ultrasound Imaging System," both filed Dec. 14, 2006 and both of which are incorporated herein by reference in their entirety.

Information obtained from the ultrasound transducer elements 126 is processed by the ultrasound equipment 150 to generate images which can be stored and displayed on a monitor for review by a clinician. The ultrasound equipment 150 will generally include a programmable processor, such as a workstation computer, operating software for controlling the operation of beam former circuits and receiving and processing ultrasound data to generate ultrasound images. The operating software will also include user-interface modules for presenting a menu of control options and implementing user inputs. The ultrasound equipment 150 may also a display for presenting ultrasound images to the user, and user input devices, such as a keyboard and pointing device (mouse, light pen and/or touch screen display) for receiving user commands and inputs. Ultrasound processors and software modules are well known in the intracardiac ultrasound imaging arts, an example of which is the ViewMate® Intracardiac Ultrasound System available from EP MedSystems, Inc. of West Berlin, N.J.

As useful as such intra-organ images can be to a clinician, the images obtainable from a catheter mounted ultrasound imaging system are necessarily limited to two dimensional slice (i.e., cross-sectional) images. This limitation to two-dimensional imaging results from dimensional limitations inherent in a catheter ultrasound imaging instrument. On the one hand, an imaging catheter must be less than about 10 French (3.3 mm) in size in order to safely access the interior of human organs, such as the heart. A catheter of a larger diameter could present clotting and flow-blockage risks to the patient. Also, larger diameter catheters are more difficult to bend through the arteries or veins by which access to an organ is obtained. On the other hand, piezoelectric transducers are limited to a minimum size range by the ultrasound frequencies desired for imaging purposes. In the intracardiac imaging application, desired ultrasound frequencies range from 3 to 10 MHz, and typically range between 5 and 7 MHz. In order to be able to produce ultrasound within this frequency range, each transducer element must have a minimum dimension (length, width and height) of approximately 0.2 square millimeters. As a result of these two dimensional limitations (i.e., catheter diameter and minimum transducer dimension), the only configuration possible for a phased array of piezoelectric transducers in an intracardiac catheter is a linear array aligned with the long axis of the catheter. A conventional intracardiac linear phased array ultrasound imaging catheter is shown in FIG. 1.

A linear phased array can only generate a two dimensional slice image by steering the ultrasound beam up and down along (i.e., parallel to) the long axis of the array. Consequently, a linear phased array ultrasound imaging catheter acquires a two-dimensional image with an image plane parallel to the long axis of the catheter. Thus, it is not possible to deploy an ultrasound imaging phased array transducer within a catheter that is capable of generating a three-dimensional ultrasound image.

While the images from an ultrasound imaging catheter can be very useful for a variety of diagnostic purpose, the two-dimensional slice image they provide shows only a small cross-section of the heart at a time. If the transducer array is oriented to view a cross section of the heart that contains healthy tissue, the clinician may not detect adjacent tissue which is behaving abnormally or is diseased. In order to view most or all of a complex three-dimensional organ such as the heart, the clinician must manually rotate the catheter in order to change the rotational orientation of the ultrasound transducer so as to scan the image plane over the organ. Further, as the heart beats, the surfaces of the ventricles and atria move in a complex motion fashion. Thus, it is difficult for a clinician to visualize the entire heart or comprehend how the various structures are moving through out the cardiac cycle when the clinician is only able to view a single thin slice image at a time. In addition, for some diagnostic applications it will be advantageous to generate three-dimensional images in order to view significant portions of an organ at the same time.

To overcome the limitations of a two-dimensional imaging capability, clinicians will typically rotate the catheter my hand during an examination in order to view different parts of the heart. By rotating the catheter back and forth, a clinician can scan the inside of the heart, similar to swinging a flashlight back and forth to view a dark room.

While this procedure allows the clinician to image much of the heart, this manual solution is necessarily limiting in utility for at least four reasons.

First, manual rotation of the catheter adds complexity to a delicate procedure that involves placement of one or more catheters directly into the patient's heart. Typically, the clinician will be controlling the angular deflection of the catheter by moving a controller on the base of the catheter, positioning the catheter within the heart by inserting or withdrawing the catheter, adjusting ultrasound imaging parameters, viewing the resulting ultrasound images, and monitoring the patient's condition, while at the same time trying to mentally assemble the image slices to "see" the whole heart and search for diagnostically significant details in the images. Manually rotating the catheter requires the clinician to master a third axis of dexterity.

Second, the clinician must rely upon memory to piece together the various views obtained in each of the two-dimensional slices in order to visualize the three-dimensional structure of the heart. This procedure may be facilitated in offline analysis when multiple adjacent images may be displayed on a computer screen simultaneously. However, such methods have limitations since it is difficult to visualize a three-dimensional image of an organ as complex as the heart, and because the viewing perspective (i.e., position and orientation) of the imaging transducer may change from image to image.

Third, the heart is a dynamic organ, moving and changing shape several times per second. Consequently, as the ultrasound imaging transducer is rotated to a new viewing angle, it is imaging the heart at different instants in the cardiac cycle. The clinician may attempt to overcome this disadvantage by slowly rotating the catheter so that images covering multiple beat cycles are obtained at each orientation. However this further complicates the clinician's task by requiring visualization of the three-dimensional structure which is changing shape constantly.

Fourth, when the clinician manually rotates the catheter, the position and angular orientation of the transducer array may move in an unpredictable manner. This is due to the fact that the catheter is bent through one or more angles in order to position it at the appropriate location in the heart for diagnostic imaging. In particular, the tip of the catheter containing the transducer array may be held at an angle by steering wires in the catheter controlled by an actuator in the catheter handle. Consequently, rotating the catheter may cause the transducer to shift laterally in position and/or rotate upward or downward with respect to the previous viewing orientation. Also, pressure from movement of the heart or blood flow may cause the transducer array to move from image to image. Consequently, a clinician is unable to know whether changes in location of imaged structures viewed in subsequent two-dimensional slicing images are the result of the shape of the heart structure, movement of the transducer array with respect to the structure, or the desired rotation of the transducer array.

As result of these difficulties, current intracardiac ultrasound catheter imaging systems have limited ability to generate three-dimensional images of the heart. Methods for correlating ultrasound images in time, particularly with respect to the cardiac cycle, have been disclosed in U.S. Patent Publication No. 2005/0080336, which is incorporated herein by reference in its entirety.

Thus, there is a need for an ultrasound imaging catheter capable of rotating the ultrasound imaging transducer about the catheter long axis with minimal effort by the clinician. Additionally, there is a need for ultrasound imaging catheter that is capable of generating ultrasound images from known perspectives reliably to facilitate multidimensional image generation with minimal impact on the clinician's efforts. While cardiac imaging represents a particularly urgent need for such catheter imaging systems, such systems could also be useful in the examination of other organs.

The various embodiments provide an ultrasound imaging catheter which includes a stepper motor that rotates the imaging transducer array to allow the physician to obtain a pan of images spaced about the catheter longitudinal axis that can then be used to produce composite images of the adjacent tissue. The embodiments include a dynamic ultrasound imaging catheter with a control mechanism for rotating the phased array ultrasound transducer within the catheter body when positioned within the heart or other organ of a patient. This transducer array rotating capability enables the clinician to scan the heart and/or obtain sufficient images through a variety of viewing angles in order to generate three-dimensional ultrasound images of the heart while reducing the workload of the clinician.

Referring to FIG. 3, an embodiment of an ultrasound imaging catheter 1 including an ultrasound imaging assembly 3 at the distal end of the catheter body 10 and a control/manipulation handle assembly 2 at the proximal end. The ultrasound imaging assembly 3 includes a linear phased array transducer 31 positioned within an ultrasound-transparent window formed by a fluid filled gap 32 and an acoustically compatible tip portion 33. The linear phased array transducer 31 can be mechanically coupled to a bearing assembly 35 which fits tightly to the catheter body 10, and electrically connected to a wire harness 13 which conducts electrical signals to and from the ultrasound system 150. A rotational drive motor 25 at the proximal end of the catheter, such as in the handle assembly 2, provides a rotational force (e.g., a torque or tension on a wire) to rotate the linear phased array transducer 31 about its long axis. In the embodiment illustrated in FIG. 3, a drive wire 36 mechanically couples the linear phased array transducer 31 to the drive motor 25 in the handle assembly 2. The rotational drive motor 25 is electrically connected by wires 26 to control circuitry (shown in FIG. 13) which may be controlled by the clinician through buttons 23, 24 on the handle assembly 2. Two (or more) steering wires 11, 12 connect to attachment points 14, 15 near the distal end of the catheter body 10 (e.g., on the proximal side of the bearing assembly 35) and to a deflection manipulator 22 on the handle assembly 2. In the embodiment illustrated in FIG. 3, the deflection manipulator 22 includes a wheel 28 coupled to a spool 29 to which the steering wires 11, 12 are connected. The wiring harness 13 passes through the handle assembly 2 and electrically connects to conductors in a cable 21 which connects the catheter assembly 1 to an isolation box 130 coupled to the ultrasound system 150. The cable 21 also includes leads for powering the drive motor 25 and communicating data regarding the transducer rotational orientation to the ultrasound system 150.

In the embodiment illustrated in FIG. 3, torque applied by the drive motor 25 is transmitted to the transducer array 31 by a drive wire 36. The drive wire 36 is made of a material with a diameter sufficient to be flexible yet resist kinking or twisting under torsion. Specifically, the drive wire 36 needs to be sufficiently flexible so the catheter can bend enough so it can pass through the patient's body and into the heart. At the same time, the drive wire 36 needs to be sufficiently resistant to bending to be able to transmit sufficient torque to rotate the transducer array 31 without twisting into a knot or kink. As used herein, the term "critical torque" refers to the torque applied to the drive wire 36 beyond which the wire may twist, kink or deform into a knot. Thus, the drive wire 36 should be of a design (i.e., material and/or configuration) that has a critical torque that is greater than the minimum torque required to rotate the transducer array 31. To meet these requirements, the drive wire 36 may be a small diameter tube, may be made of a high strength, flexible metal such as titanium, and/or made of a material having directional strengthening elements (e.g., carbon nanotubes) within the wire material to provide preferential deflection characteristics.

In embodiments employing a drive wire 36, the transducer array 31 is rotated about its long axis by applying a torque to the drive wire 36 using the drive motor 25 positioned at the proximal end of the catheter, such as in the handle assembly 2. To enable the transducer array 31 to rotate in response to the applied torque, the transducer array 31 may be mounted on a proximal bearing 35 which allows the transducer array 31 to rotate with respect to the catheter body 10. Sufficient slack is provided in the wire harness 13 so that the wires can twist within the catheter body 10 as the transducer array 31 turns without binding the rotation or pulling an individual wire out of the transducer array. Since the transducer array 31 is rotated approximately 30 to 90 degrees one direction and then 30 to 90 degrees in the other direction, the slack in the wire harness 13 only needs to be sufficient to permit a quarter rotation or less.

Details of an embodiment of the ultrasound imaging assembly 3, including the transducer array 31 and bearing 35, are shown in FIGS. 4A and 4B. Referring to FIG. 4A, the transducer array 31 can be coupled to the inner portion of the bearing 35 so that it does not touch the inside surface of the window portion 33. So supported, the transducer array 31 can freely rotate within the fluid filled gap 32 without rubbing the transducer elements 326 or support structure 322 against the window portion 33 of the catheter 1. Permitting the transducer array 31 to rotate within a fluid filled gap 32 prevents the array from damaging the window portion 33 (such as scoring the inside) and the window portion 33 from damaging the transducer elements 326 during rotation. Also, the acoustic path between transducer elements 326 and the patient will remain the same as the transducer array 31 rotates.

Fluid within the fluid filled gab 32 provides consistent acoustic coupling between the transducer elements 326 and the acoustic window portion 33 of the catheter 1. Conventional ultrasound imaging catheters are designed to avoid gaps between the transducer elements and catheter body, since such gaps will inhibit sound transmission. Also, conventional ultrasound imaging catheters do not include fluid within the catheter, since fluids may cause shorting of electronics. Thus, the inclusion of an acoustic coupling fluid within the catheter in the ultrasound imaging assembly 3 region represents a marked departure from past practice. This acoustic coupling fluid may be selected to have a speed of sound that is compatible (i.e., nearly the same as) that of the acoustic window portion 33 of the catheter, which maximizes the coupling of ultrasound energy between the transducer elements 326 and the exterior of the acoustic window portion 33. Suitable acoustic coupling fluids include, for example, mineral oil, degassed water, and degassed saline solution.

Three alternative embodiments are described herein for providing the acoustic coupling fluid to the window portion 33 of the catheter, although other methods may be used and are encompassed within the scope of the present invention. In a first embodiment, the acoustic coupling fluid is added to the window portion 33 when the catheter is assembled. In a second embodiment, the acoustic coupling fluid is added to the window portion 33 just prior to usage, such as by a clinician. In a third embodiment, the acoustic coupling fluid is sterile saline solution which is injected into the proximal end of the catheter assembly to flow through the catheter and out the distal end of the window portion 33 during use.

In the first embodiment wherein the acoustic coupling fluid is added during manufacture, various sealing and fluid expansion features are necessary as discussed herein with respect to various embodiments. Also, consideration must be made for evaporation and/or degradation of the acoustic coupling fluid during shipping and storage prior to use. For example, water or saline solution may evaporate over time, so mineral oil may be preferred for this embodiment. However, mineral oil presents added safety concerns which may require additional design features, such as employing double walls in the portion of the catheter containing the fluid.

In the second embodiment in which the acoustic coupling fluid is added by a clinician just prior to use, the distal cap 211 can be configured so that the clinician can securely attach the cap 211 after filing the window portion. The sealing mechanism may be any known mechanism, including a threaded connection, a snap fit, a bayonet fit, and/or an adhesive. In this embodiment, the clinician can inject the coupling fluid, such as sterile saline solution by holding the window portion vertically, with distal end up, pouring or injecting (e.g., with a syringe) the fluid into window portion 33, and then sealing the catheter by attaching the distal cap 211. A funnel or other filling aid may be provided to assist the clinician. Care must be taken not to inject the saline solution under pressure since dissolved gas may then form bubbles within the window portion 33 during operation, which would degrade imaging performance.

In the third embodiment where a stream of sterile saline solution flows through the catheter during use, the catheter assembly includes a port on the handle portion 2 for connecting to a saline source and an opening or vent on the distal tip of the window portion 33 through which saline solution exits the catheter. Any of a number of known ports for coupling a saline source to a catheter may be used in this embodiment. A shipping/storage cap (such as the distal cap 211 shown in FIGS. 12A, 12B) may be attached to the distal tip of the catheter during assembly to protect the vent from contamination, with the cap configured to be removed by the clinician just prior to use. In this embodiment, the clinician may prepare the catheter assembly by coupling the port to a saline source, removing the shipping/storage cap, establishing saline flow until a steady stream free of bubbles exits from the distal vent, and then inserting the catheter into the patient. During operation the saline solution flows into the patient. Otherwise, the operation of this embodiment is similar to the various other embodiments. Since the ultrasound imaging catheter is a single use instrument, the catheter components need only resist the effects of saline (e.g., corrosion) for the duration of the examination session.

In an embodiment, a partial acoustic window 332 may be provided over the portion of the catheter through which ultrasound will be transmitted. In this embodiment, a particularly thin window or a window of a different material may be provided to facilitate ultrasound transmission. For example, in an embodiment where the transducer array 31 is rotated through 60 degrees, the partial acoustic window 332 would be provided over the 60-70 degrees portion of the circumference of the catheter through which ultrasound may be transmitted. This embodiment enables the rest of the acoustic window portion 33 to be made thicker or from a more rigid material so that the end portion of the catheter can have sufficient structural rigidity for its intended use and a partial acoustic window 332 with desired acoustic properties.

In order to achieve desired acoustic coupling with blood and tissue, the material used to make the partial acoustic window 332 may be selected to have a speed of sound that is nearly the same as that of blood. A suitable material for this purpose is Mylar® polyester film. Alternatively, the acoustic window can be made from other materials, such as Pebax® polyether block amide used for the rest of the catheter, provided the window thickness is one-fourth the ultrasound wavelength or less.

Figure 4C:
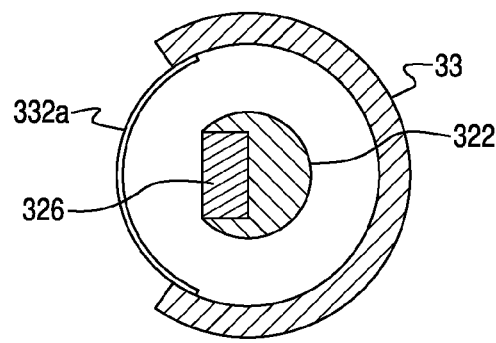
FIGS. 4C-4E are transverse cross sectional views of alternative embodiments of the distal end of the ultrasound imaging catheter shown in FIG. 3.

FIG. 4C shows a cross sectional view of the window portion 33 for an embodiment employing a Mylar® window 332a. To manufacture this embodiment, an opening is cut into the window portion 33 spanning the desired viewing angle and extending longitudinally along the length of the transducer array 32. A Mylar® sheet window 332a is then plastic weld, bonded or glued onto the window portion 33 (such as on the inside surface as illustrated) so as to close the opening and form the window 332a. The acoustic coupling fluid within the window portion 33 will maintain the shape of the Mylar® window 332a in use.

Figure 4D:
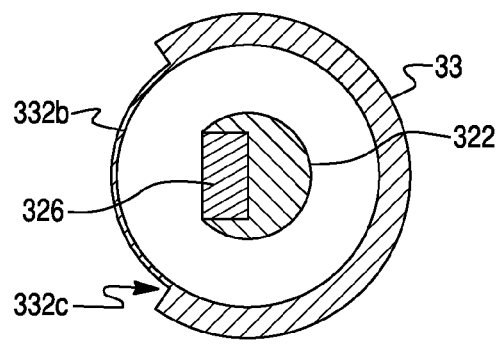

FIG. 4D shows a cross sectional view of the window portion 33 for an embodiment employing a quarter-wave Pebax® window 332a. To manufacture this embodiment, a reduced thickness portion is machined (e.g., by laser machining) or etched into the window portion 33 spanning the desired viewing angle and extending longitudinally along the length of the transducer array 32. Alternatively, the window portion 33 may be formed (e.g., by injection molding or extrusion) with the reduced thickness portion as illustrated in FIG. 4D.

In an alternative embodiment, the acoustic window portion 33 of the end of the catheter is the same all around. This may be accomplished by limiting the thickness of the window portion 33 walls to one-quarter wavelength, which would enable the window portion 33 to be made from a variety of materials, including Pebax®, or by manufacturing the window portion 33 from a material having a speed of sound close to that of blood, such as Mylar®. This embodiment simplifies assembly of the catheter assembly since the transducer array 31 need not be rotationally aligned when inserted into the catheter body 1.

To enable fabrication of the catheter assembly, the distal end of the catheter body 10 may be sealed with a distal cap 211. In this manner, the catheter body 10 may be slipped over the transducer array 31, wire harness 13, drive wire 36 and other internal elements during assembly, and then sealed by gluing or bonding the distal cap 211. In an embodiment, the fluid filled gap 32 is filled with the acoustic coupling fluid just prior to sealing the catheter body with the distal cap 211.

In order to suspend the transducer array 31 within the fluid filled gap 32, the bearing 35 may be of sufficient height (i.e., length along the centerline) and landed on a bearing seat 350 portion of the catheter body 10 to resist deflection of the transducer array 31. As shown in FIG. 4A, a bearing seat 350 can be provided in the catheter body 10 with a diameter and length that matches closely that of the bearing 35. A lip 350A may be provide on the proximal end of the bearing seat 350 to assist in seating and aligning the bearing 35 and preventing the bearing 35 from slipping beyond (i.e., in the proximal direction) the bearing seat 350 during assembly or operation. When the bearing 35 and bearing seat 350 are tightly coupled, such as by way of a compression fit (i.e., the inner diameter of the bearing seat 350 is slightly smaller than the outer diameter of the bearing 35) or adhesive, the assembly forms a cantilever joint sufficient to resist bending loads from the transducer array 31 and thereby keep the array approximately centered within the fluid filled gap 32.

FIG. 4B illustrates an alternative embodiment in which a second, distal bearing 37 is provided to support the distal tip of the transducer array 31 within the acoustic window portion 33 of the catheter. (To avoid confusion, subsequent references to the bearing 35 positioned on the proximal end of the transducer array 31 will identify it as the "proximal bearing 35" even though some embodiments will only include one bearing.) Suspended between the distal bearing 37 and the proximal bearing 35, both of which contact an inner surface of the catheter, the transducer array 31 can be centered in the fluid filled gap 32 and prevent from contacting the acoustic window portion 33 of the catheter. The distal bearing 37 can seat on a portion of the distal cap 211 (as shown) or on a seat provided on the acoustic window portion 33 (not shown). This embodiment reduces the dimensional requirements on the bearing seat 350 since the joint formed between the proximal bearing 35 and the bearing seat does not need to resist cantilever bending loads.

Figure 4E:
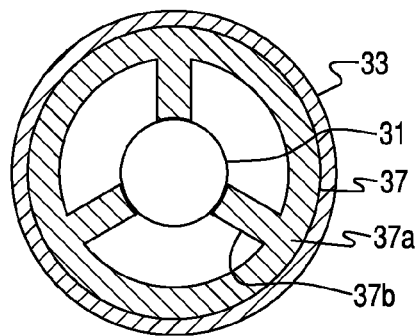
Figure 9:
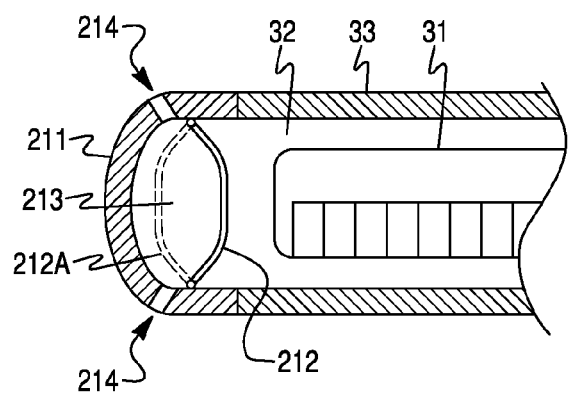
FIG. 9 is a cross section view of the distal tip of the dynamic ultrasound imaging catheter showing an example implementation detail.

FIG. 4E illustrates an alternative configuration for a distal bearing 37. In this configuration, the distal bearing 37 includes a ring 37a that contacts the inner surface of the window portion 33, with three (or more) posts or pads 37b extending radially inward toward the centerline a distance sufficient to come in contact with the distal tip of the transducer array 31. The pads 37b ensure that the tip of the transducer array 31 remains approximately centered in the window portion 33 while allowing the transducer array 31 to rotate. The pads 37b may be made from a low friction material such as Teflon®. Gaps between the pads 37b then permit fluid to pass through the distal bearing 37. This feature will ensure lubrication of the pads 37b and help enable the functioning of a fluid expansion membrane 212 as illustrated in FIG. 9.

Figure 5A:
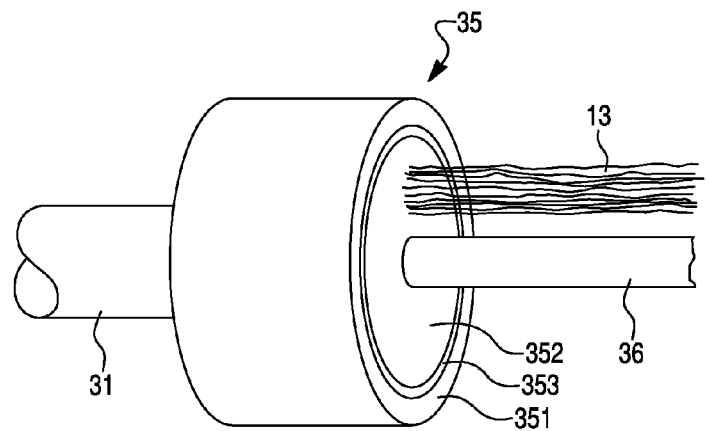
FIGS. 5A and 5B are perspective views of an embodiment of a bearing assembly suitable for use in the dynamic ultrasound imaging catheter shown in FIG. 3 shown in FIG. 3
Figure 5B:
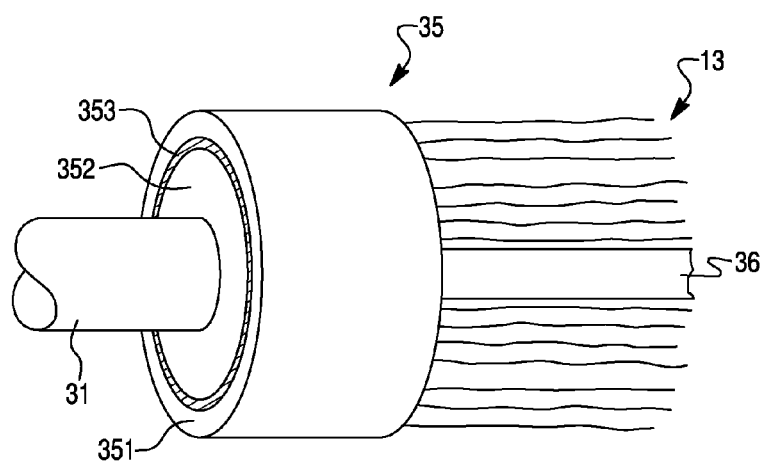

In addition to supporting the proximal end of the transducer array 31, the proximal bearing 35 may be used as a fluid seal to prevent the acoustic coupling fluid within the fluid filled gap 32 from leaking into the catheter body 10 in some embodiments. This may be accomplished using a slip bearing such as illustrated in FIGS. 5A and 5B. In the illustrated embodiment, the proximal bearing 35 includes an outer bearing ring 351 and an inner bearing plug 352 separated by a low friction bearing surface 353. The bearing surface may be made from a low friction material such as Teflon®, which may be a separate piece (e.g., a thin Teflon cylinder) or a surface coating applied to one or both of the outer bearing ring 351 and inner bearing plug 352. When assembled, the low friction bearing surface 353 permits the inner bearing plug 352 to turn freely with respect to the outer bearing ring 351, yet forms a relatively fluid-tight seal through the bearing. Additionally, this simple bearing configuration is easier to assemble than bearings involving rollers or balls, particularly in the diameter suitable for use in a 10 French or smaller catheter.

In the embodiment illustrated in FIGS. 5A and 5B, the inner bearing plug 352 forms an intermediary structure between the transducer array 31 on the distal side and the wire harness 13 and drive wire 36 on the proximal side. Thus, in this embodiment, the drive wire 36 is connected to the inner bearing plug 352 so that torque is transferred from the drive wire 36 to the plug body on the proximal side of the bearing 35 (shown in FIG. 5A), and from the plug body to the transducer array 31 on the distal side of the bearing (shown in FIG. 5B). This connection may be any mechanical or structural connection sufficient to withstand the critical torque. For example, the drive wire 36 may be mechanically connected to the plug body by a threaded connection (such as a threaded sleeve over the wire), a latching mechanism, tying or wrapping the wire over a connection piece (e.g., an eyelet), or other known mechanical connection, or welded, braised or glued to the plug body, or a combination of both means.

The plug body may also serve as an electrical pathway for the individual coaxial wires in the wire harness 13 to the transducer array. In a simple configuration, the wires of the wire harness 13 pass through the plug body and connect to the transducer array. This structure avoids fluid paths along wires in the plug body between the fluid filed gap 32 and the rest of the catheter.

By way of example, the inner bearing plug 352 may be formed by over the proximal end of the transducer array 31 and a portion of the wire harness 13 after the electrical connections have been established and confirmed. The plug body may be formed of molded plastic poured over the end of the transducer array 31 and the connected wires, and then polished to the required dimensions. A ring of harder material (e.g., a thin metal cylinder) may be slipped over the plastic plug body to form a bearing surface. By forming the inner bearing plug 352 in this manner, the plug body can help ensure the integrity of electrical connections to the transducer array 31 are maintained while the array is rotated.

Figure 7A:
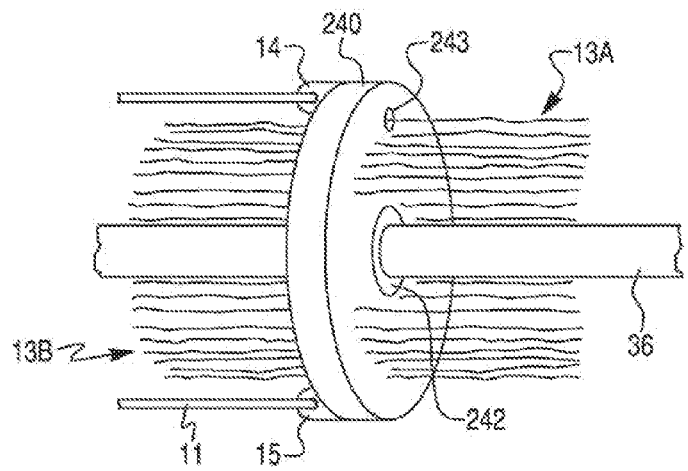
FIGS. 7A-7C are perspective views of details of the alternative embodiments illustrated in FIGS. 6A and 6B.
Figure 7B:
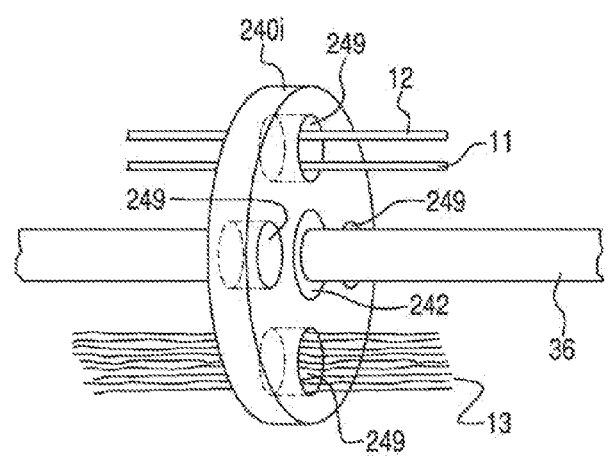
Figure 7C:
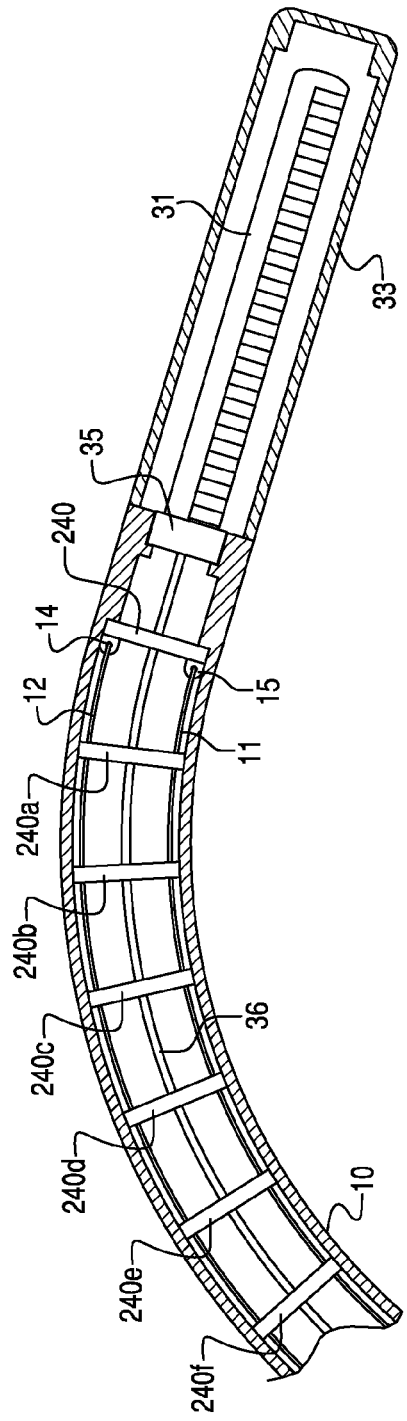
Figure 8:
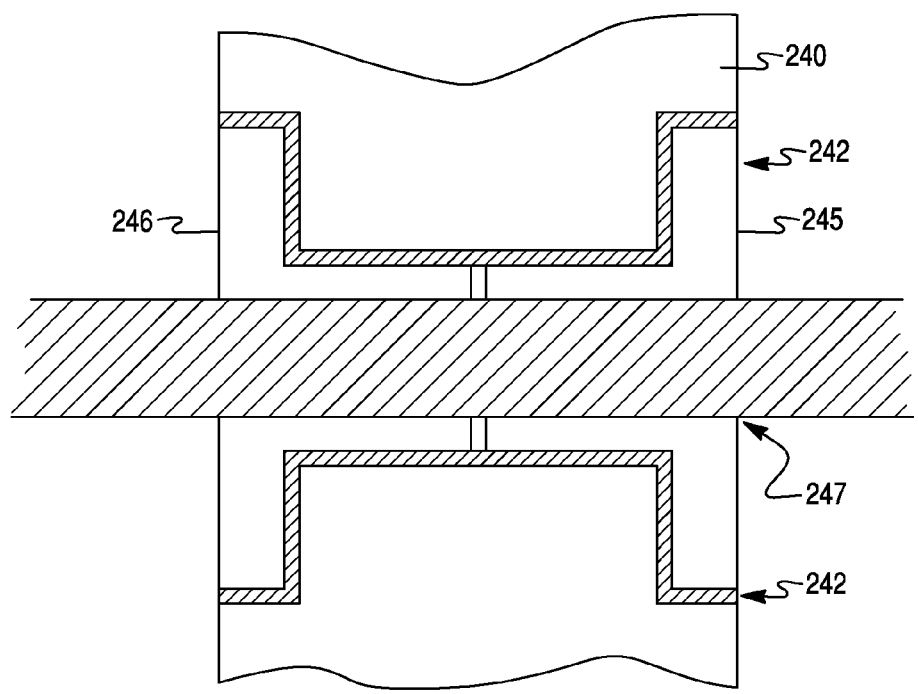
FIG. 8 is a cross section view of a portion of the detail illustrated in FIG. 7.

Another embodiment of the ultrasound imaging assembly 3 is illustrated in FIGS. 6A and 6B. In this alternative, a second fluid seal in the form of a divider disc 240 is provided on the proximal side of the proximal bearing 35. This alternative embodiment is applicable to both the single bearing embodiment shown in FIG. 6A and the dual bearing embodiment shown in FIG. 6B. Details of the divider disc 240 are illustrated in FIGS. 7 and 8. Therefore, reference is made to FIGS. 6A, 6B, 7A-C and 8 in the following description of this alternative embodiment.

Positioning a divider disc 240 proximally removed from the proximal bearing 35 can serve a number of design purposes. For one, the divider disc 240 can serve as the structure to which the steering wire anchors 14, 15 attach (as shown in FIG. 7A, or as the anchor points (such as holes near the edge of the disc through which or to which the steering wires 11, 12 are attached). By affixing the divider plate 240 to the catheter body 10, such as by seating it against a lip or ridge 241 on the interior of the catheter body 10, bending forces applied by the steering wires 11, 12 can be conveyed to catheter. By positioning the divider disc 240 a small distance from the proximal bearing 35, the bearing and bearing seat 350 can be isolated from distortions in the catheter body 10 due to bending. Thus, catheter bending can be limited to portion 202 of the catheter while the region 201 between the divider disc 240 and the proximal bearing 25 remains relatively straight and undistorted. The divider disc 240 can be made from a number of stiff materials, such as Pebax®.

The divider disc 240 can also serve as a second or primary fluid seal to retain acoustic coupling fluid on the distal side of the disc. This can be accomplished, for example, by passing the wires of the wire harness 13 through the disc in fluid-proof seals 243 and providing a fluid tight shaft seal 242 around the drive wire 36. Passing the wires through divider disc 240 results in two portions of the wire harness 13, a distal wire harness 13A and a proximal wire harness 13B. To allow for rotation of the transducer array 31, the distal wire harness 13A should have sufficient extra length to twist through the angle of rotation of the transducer. On the other hand, the proximal wire harness 13B will not experience twisting.

Referring to FIG. 8, a low friction bearing and fluid-tight shaft seal 242 may be formed, for example, by sealing to the drive wire 36 a proximal inner seal plug 245 that fits in the proximal side of a through hole 247 in the divider disc 240 and distal inner seal plug 246 that fits in the distal side of the through hole 245 in the divider disc 240. A low friction layer 248 may be provided between the two seal plugs 245, 246 and the divider disc 240 to minimize rotational friction.

In an embodiment, the catheter may be provided with a number of centering discs 240i (such centering discs 240a through 240f as illustrated in FIG. 7C) that are similar to the divider disc 240. Referring to FIG. 7B, centering discs 240i may be fashioned as a disc with a diameter approximately equal to the inner diameter of the catheter body 10, having a central low friction bearing 242 such as that described above with reference to FIG. 8. Since the centering discs 240i may not be fluid boundaries, they may include through holes 249 (e.g., three or four holes as illustrated in FIG. 7B) through which the wire harness 13 and steering lines 11, 12 can be threaded. In embodiments in which the entire catheter 1 is filled with the acoustic coupling fluid, such as the embodiments in which sterile saline solution is continuously injected into the proximal end of the catheter during use, the through-holes 249 provide paths for the acoustic coupling fluid to pass.

A primary function of centering discs 240i is to ensure the drive shaft 36 remains approximately centered in the catheter body 10 as the catheter is bent. Since the drive shaft 36 may have different bending characteristics, it may follow a different radius of curvature than that of the catheter body 10 through a bend. This could cause some of the rotational torque to be translated into displacement forces applied to the catheter body 10, which could result in the catheter moving during scanning operation as well as introducing errors into the transducer rotational orientation. To avoid the potential for such problems, two or more centering discs 240i may be provided at intervals along the portion of the catheter body 10 that will experience bending. As illustrated in FIG. 7C which shows six centering discs 240a through 240f in addition to the divider disc 240, the centering discs 240i help to maintain the drive shaft 36 along the centerline of the catheter body 10.

As illustrated in FIG. 7B, the through-holes 249 in the centering discs 240i can be used to separate the wire harness 13 and the steering wires 11, 12 from the drive shaft 36 to prevent tangling during oscillation operations when the drive shaft 36 will be rotating rapidly. As illustrated in FIG. 7C, the centering discs 240i can be also be used to thread the steering wires 11, 12 so they lie on the same side of the catheter body 10, which reduces the steering errors since the path length of the steering wires 11, 12 through the catheter remains the same as the catheter bends. For example, the steering wires 11, 12 may pass through through-holes 249 on opposite sides of centering discs 240a and 240b, and then be brought together so they pass through the same through-hole 249 in subsequent centering discs 240c-240f. This configuration can be used to apply proper bending torque to the divider plate 240 while passing the steering wires 11, 12 along the same side of most of the catheter body 10.

Operation of the embodiment illustrated in FIGS. 6A, 6B, 7A-C and 8 is similar to that of the embodiments illustrated in FIGS. 4A and 4B. Further, the centering discs 240i described above with reference to FIGS. 7B, 7C may be implemented with the embodiments illustrated in FIGS. 4A and 4B.

In the various embodiments which include a sealed catheter assembly wherein the acoustic coupling fluid is provided during manufacture, provisions must be made to accommodate expansion/contraction of the acoustic coupling fluid with temperature changes. Operation of the transducer elements 326 will heat the acoustic coupling fluid, which will cause the fluid to expand. During shipping and storage, the catheter may be subjected to cold temperatures (e.g., while be shipped during the winter) which will cause the acoustic coupling fluid to contract, as well as hot temperatures (e.g., while being shipped during the summer months) which will cause the acoustic coupling fluid to expand. To avoid damage to the transducer array 31, bearings 35, 37 and acoustic window portion 33 of the catheter, a fluid reservoir can be included to accept excess fluid when the fluid expands and ensure the fluid filed gap 32 remains filled when the fluid contracts. To a certain extent, fluid volume changes can be accommodated by flexure of the acoustic window portion 33 of the catheter.

An example of a fluid expansion reservoir is illustrated in FIG. 9. In this example embodiment, the catheter distal cap 211 includes a flexible expansion membrane 212 which can flex into and out of an expansion volume 213 within the distal cap 211. Vent holes 214 in the distal cap 211 allow air or fluids to pass through the cap to accommodate displacement of the expansion membrane 212. In this example, the expansion membrane 212 extends into the fluid filled gap 32 when the acoustic coupling fluid is cold (i.e., at minimum volume), and expands outward into the expansion volume 213 (such as to extended position 212A) as the acoustic coupling fluid heats up. By controlling the size and shape of the expansion membrane 212 and size of the expansion volume 213, the maximum and minimum volumes of the acoustic coupling fluid can be accommodated. Other fluid reservoir and expansion mechanisms known in the mechanical arts may also be used. It is worth noting that the presence of the acoustic coupling fluid in the catheter will require use of non-thermal methods of sterilization, such as chemical cleaning and/or gamma irradiation.

While the foregoing embodiments include fluid seals in the proximal bearing 35 and/or divider disc 240 to retain the acoustic coupling fluid in the distal portion of the catheter, in other embodiments the entire catheter can be filled with fluid. These embodiments simplify fabrication by eliminating the need for providing fluid-tight seals in the vicinity of the transducer array 31. In one of these embodiments, one or more fluid boundary seals, like the divider disc 240 illustrated in FIGS. 6A, 6B, 7A and 8, are positioned near the proximal end of the catheter body 10 to prevent the acoustic coupling fluid from reaching the handle. In another embodiment, the acoustic coupling fluid fills the entire catheter and a portion of the handle assembly 2 including the drive motor 25 and the deflection spool 29. These alternative embodiments may not require volume compensation mechanisms, since the expansion of the acoustic coupling fluid with temperature can be accommodated by elastic expansion of the entire catheter body 10.

While the foregoing embodiments employ a drive wire 36 to transfer rotational torque to the transducer array 31, other mechanisms for rotating the transducer array 31 may be used. For example, FIGS. 10A-10E and 11A-11E show alternative embodiments in which the rotational force is provided from a drive motor 25 in the handle assembly 2 to the transducer array 31 by tension lines 361, 362 which wrap around one or two drive spools 368, 369 coupled to a short drive wire 336 that transmits torque to the array.

Figure 11A:
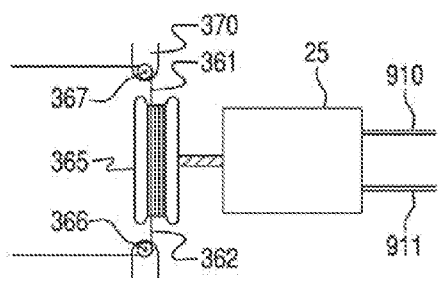
FIGS. 11A-11E are cross sectional views of alternative embodiments of the drive motor portion of the handle of the dynamic ultrasound imaging catheter.

Referring to FIG. 11A, rotational energy from the drive motor 25 turns a drive motor spool 365 which transfers the rotational energy into tension in tension lines 361, 362 wrapped about the drive motor spool 365. When the drive motor spool 365 turns in one direction, tension line 361 is pulled toward the handle, for example, while tension line 362 is play out away from the handle an equal amount. Similarly, turning the drive motor spool 365 in the opposite direction applies tension to tension line 362 while playing out tension line 361. Line guiding structures, such as pulleys 366, 367 mounted on the handle assembly 1 by structures 370, may be use to direct the drive wires into the catheter body 10, although the drive motor spool 365 may be oriented so no pulleys are necessary.

Figure 10D:
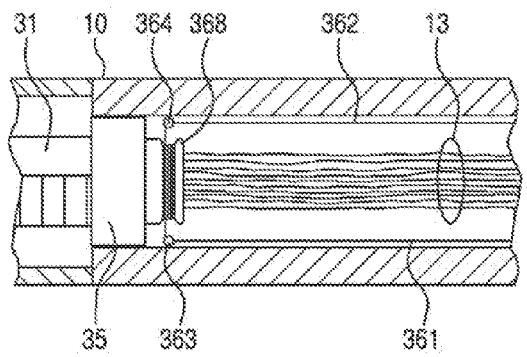

Near the distal end of the catheter 1, the tension lines 361, 362 pass through turning blocks 363, 364 which direct the tension lines 361, 362 onto one drive spool 368, in the embodiments shown in FIGS. 10B-10D, or two drive spools 368, 369, in the embodiment shown in FIG. 10A. The tension lines 361, 362 are wound onto the drive spool 368 (or drive spools 368, 369) so that when tension is applied to one of the tension lines 361 or 362, the drive spool 368 (or 369) turns to play out line. As the tension line 361 or 362 turns the drive spool 368 (or 369), torque is applied to a short drive shaft 366 coupled to the drive spool 368, (or drive spools 368, 369) which transmits the torque to the transducer array 31 through a bearing 35 in the manner described above. The proximal end of the short drive shaft 366 may be supported in the catheter body 10 by a proximal drive shaft bearing 365 in order to resist bending forces due to tension on one tension line or the other. Grooves or through holes in the proximal drive shaft bearing 365 may be provided to allow the drive wires 361, 362 to pass through the bearing to reach the turning blocs 363, 364.

In the embodiment illustrated in FIG. 10A, each tension line 361, 362 is wound onto its own drive spool 363 or 364. The tension lines are wound in different directions, so when one tension line (e.g., 361) is pulled causing it to unwind from its drive spool (e.g., 369), the other tension line (e.g., 362) is wound onto its drive spool (e.g., 368). The wire harness 13 passes through drive spools 368, 369 to connect with the transducer array 31 as described above with reference to FIG. 3. Since the two drive spools are positioned adjacent to each other along the longitudinal axis, the turn buckles 363, 364 will be at different axial positions along the catheter body 10, which may allow them to be positioned on the same side of the catheter. The tension lines 361, 362 are firmly attached to their respective drive spools 368, 369 so that when fully unwound the lines do not come free from the spool.

In the embodiment shown in FIG. 10B, only a single drive spool 368 is employed, with the tension lines 361 and 362 winding onto the spool in opposite directions. In this embodiment, the tension lines 361, 362 may be a continuous line that wraps a number of times around the drive spool 368, or two separate lines each firmly attached to the spool. Since the tension lines 361 and 362 wind onto the drive spool 368 in opposite directions (and therefore on opposite sides), when the spool turns to let out one line (e.g., 361) it simultaneously winds in the other line (e.g., 362) an equal amount. Resulting torque applied to the drive spool 368 is conveyed to the transducer array 31 by the short drive shaft 366 which may be supported by a proximal drive shaft bearing 365. As with the previously describe embodiment, the wire harness 13 passes through drive spool 368 to connect with the transducer array 31 as described above with reference to FIG. 3.

While the embodiments illustrated in FIGS. 10A and 10B employ a short drive shaft 366, the rotational torque may be conveyed from the drive spool 368 to the transducer array 31 by a drive cylinder 367 as illustrated in FIG. 10C. In this embodiment, the drive cylinder 367 may encompass the wire harness and the drive spool 368 may be a ring with raised edges (to retain the drive wires 362, 362) positioned over and coupled to the cylinder. The routing and winding of the tension lines 361, 362 may be similar to that of the embodiment shown in FIG. 10B. Since the drive cylinder is hollow, the wire harness 13 can pass through the cylinder and the proximal drive shaft bearing 365 to connect with the transducer array 31 as described above with reference to FIG. 3.

The proximal drive shaft bearing 365 shown in FIGS. 10A-10C helps to stabilize the drive shaft 366 or drive cylinder 377 within the catheter body 10 and resist bending forces applied by the tension lines 361, 362. However, the proximal drive shaft bearing 365 may be dispensed with in embodiments where the proximal bearing 35 and short drive shaft 366 or drive cylinder 367 are rigid enough to resist the cantilever bending forces applied by the tension lines 361, 362. For example, in an embodiment shown in FIG. 10D, the drive spool 368 can be directly coupled to the inner bearing plug 352 of the proximal bearing 35 so the bending forces applied by the tension lines 361, 362 are resisted by the bearing 35 directly, thereby minimizing cantilever bending stresses. In the embodiment shown in FIG. 10D, the drive spool 368 may be glued, brazed or welded to the inner bearing plug 352, or may be an extension of the inner bearing plug 352 itself. In this embodiment, the wire harness 13 passes through the drive spool 368 and inner bearing plug 352 to reach the transducer array 31. While FIG. 10D shows a single drive spool 368, two drive spools may be employed, with a second drive spool (369) coupled to the proximal side of the first drive spool 368 and the wires routed and wound as described above with reference to FIG. 10A.

Figure 10E:
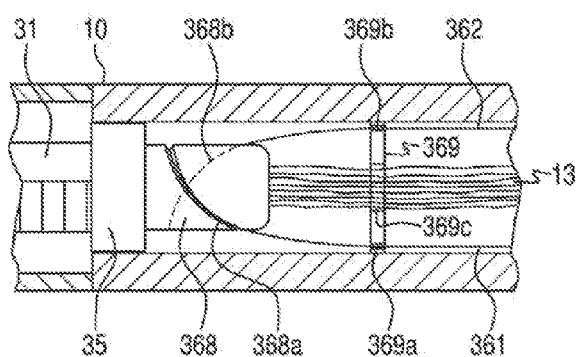

An alternative embodiment for the drive spool 368 is illustrated in FIG. 10E that obviates the need for turn buckles 363, 364. In this embodiment, the drive spool 368 includes two winding grooves 368a, 368b disposed approximately on opposite portions of the spool. A divider plate 369 is provided on a proximal side and slightly removed from the drive spool 368, with through-holes 369a, 369b near the periphery through which the drive wires 361, 362 pass. The diameter of the drive spool 368, the inclination of the winding grooves 368a, 368b, the distance between the drive spool 368 and the divider plate 369, and the radial separation between through-holes 369a, 369b are configured so that the drive wires 361, 362 experience a small angle as they exit the through-holes and wind directly onto the winding grooves 368a, 368b. So configured, the drive wires 361, 362 will play directly onto the drive spool 368 with low friction, thereby eliminating for a turn buckle or other mechanism to guide the wires onto the drive spool 368. By providing winding grooves 368a, 368b on opposite sides of the drive spool 368, oscillating motion can be induced by alternatively pulling on one drive wire 361 followed by pulling on the other drive wire 362.

Figure 11B:
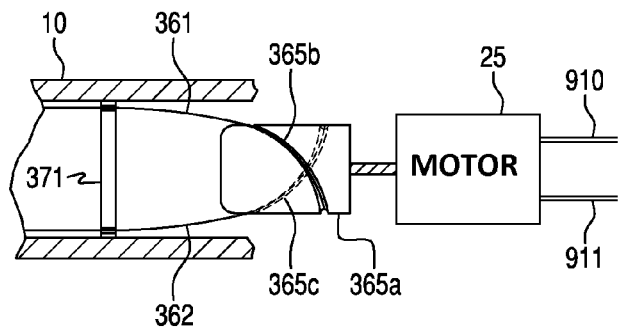

A drive spool with inclined winding grooves may also be employed on the drive motor side (i.e., proximal end of the catheter) to eliminate the need for turn buckles. Referring to FIG. 11B, the drive spool 365a coupled to the drive motor 25 can include inclined winding grooves 365b and 365c onto which the tension lines 361, 362 are threaded. By accepting the tension lines at an angle to the circumference, the turn buckles can be replaced with a divider plate 371 with through holes for directing the tension lines 361, 362 at a slight angle from the catheter on to the drive spool 365a. As with the drive spool assembly on the distal end, the diameter of the drive spool 368, the inclination of the winding grooves 368a, 368b, the distance between the proximal drive spool 365a and the divider plate 371, and the radial separation between through-holes are configured so that the drive wires 361, 362 experience a small angle as they exit the through-holes and wind directly onto the winding grooves 365b, 365c. So configured, the drive wires 361, 362 will play directly onto the drive spool 365a with low friction, thereby eliminating for a turn buckle or other mechanism to guide the wires onto the drive spool 365a. By matching the diameter of the proximal drive spool 365a to that of the distal drive spool 368, a rotation of the drive spool on the handle will result in an equal rotation of the distal drive spool and thus the transducer array.

In the various embodiments, the distal end of the catheter 1 can be deflected or steered by manipulating the deflection manipulator 22 on the handle assemble 2. Mechanisms for deflecting or steering ultrasound imaging catheters are disclosed in U.S. Patent Application Publication No. 2005/0228290, the contents of which are incorporated herein by reference in their entirety. In general, when the deflection manipulator 22 is turned (or slide for slide manipulator configurations), tension is applied to one steering line 11 while tension is eased on the other steering line 12. Tension on steering line 11 pulls on the attachment point 14 coupled to the catheter body 10 near the distal end. This tension causes the distal portion to bend toward the side in tension. Steering the other direction is accomplished by reversing the motion on the deflection manipulator 22, which places steering line 12 in tension and eases steering line 11. The attachment points 14, 15 for the steering lines 11, 12 may be provided in a number of configurations, including directly coupled to the catheter body 10, to a portion of the transducer array structure 3, to a proximal side of the bearing 35, to a ring in firm contact with the catheter body 10, or a disc (as shown in FIG. 7) in firm contact with the catheter body.

In an alternative embodiment, the catheter body 10 may include steering wires within the walls of the catheter, obviating the need to pass the steering wires through interior. Such catheters are commercially available, and therefore further description of the steering wire configurations is unnecessary.

In embodiments employing tension lines 361, 362 to transmit rotational torque to the transducer array 31, the tension lines may also be used to deflect or steer the distal portion of the catheter 1. In this embodiment, transducer array 31, bearings 35, 37 and/or the drive spool 368 include a mechanism that prevents the transducer array 31 from rotating beyond a certain angle (e.g., ±30 degrees). For example, this mechanism may be a physical stop one or in the bearing 35 or drive spool 368 like a tab on a rotating surface that engages a tab on catheter body 10 at the maximum rotation angle. As another example, the tension lines 361, 362 may be anchored to the drive spool 368 so that at the maximum rotation angle one of the tension lines 361 or 362 is completely unwound from the spool and tension is applied directly to the spool. In this embodiment, the deflection manipulator is replaced by an operational mode for the drive motor 25 which may be controlled by the buttons 23, 24 on the handle assembly 2. To deflect the distal portion of the catheter is this embodiment, the transducer array 31 is rotated to its maximum rotation angle by the drive motor 25 and then further tension is applied by the drive motor 25 to the tension line 361 or 362. With further rotation of the drive spool 368 stopped, force from the line tension will be applied to the corresponding turn buckle 363 or 364 which will apply a bending force to the catheter body 10, causing the distal portion to deflect or steer. To deflect the catheter in the opposite direction, the drive motor 25 is run in the opposite direction until the transducer array 31 is rotated to its opposite maximum rotation angle and further tension is applied, which applies a bending force to the catheter body 10 through the other turn buckle 364 or 363. It should be noted that this embodiment does not allow the deflection induced using drive wires 361, 362 to be maintained during ultrasound scanning. Therefore, this deflection mechanism may be used in conjunction with the steering wire deflection mechanism described herein with reference to FIG. 3, such as to provide a second plane of deflection useful during the catheterization process. Also, electronic measures may be implemented to prevent the drive motor 25 from turning the transducer array 31 to the rotational stops during ultrasound imaging in order to prevent inadvertent deflection of the ultrasound imaging assembly 3.

A variety of drive motors 25 and motor configurations may be used in the various embodiments. In one embodiment, the drive motor 25 is a stepper motor that allows for precise control of the rotation of the drive shaft as the motor moves one angular increment (i.e., step) at a time. In this embodiment, the drive motor 25 can be advanced a single step or a few steps and then held in that orientation while one or more ultrasound frames are obtained, before being advanced to the next step (or few steps). The drive motor 25 may alternatively be a continues motion motor, in which case an orientation sensor, such as an optical disc sensor, may be included in the motor assembly so the controller can determine the orientation of the drive shaft 36 or drive spool 365.

Figure 11C:
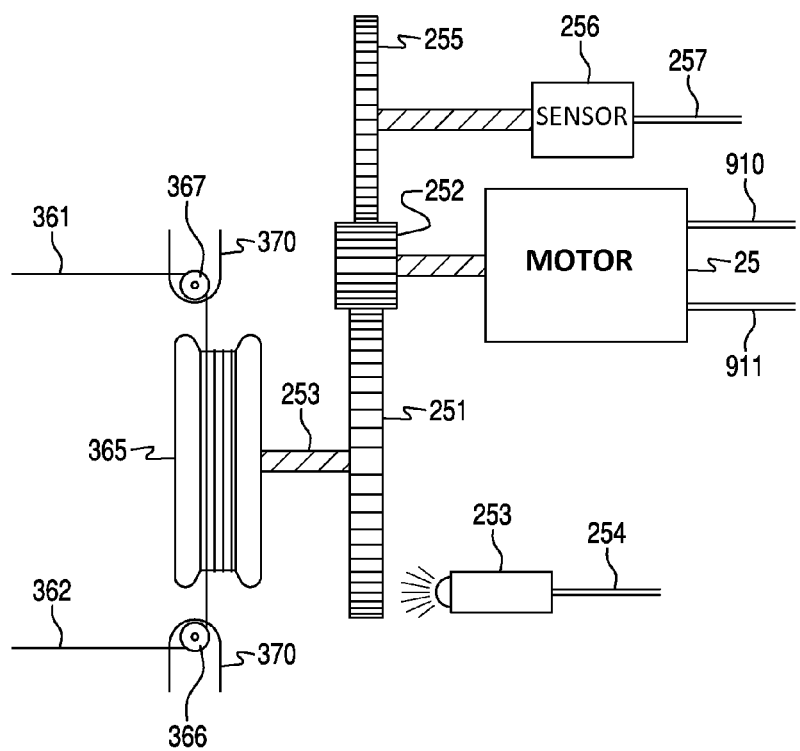

In another embodiment illustrated FIG. 11C, in the drive motor 25 may include a gearing mechanism, such as a small gear 252 coupled to the motor 25 rotor that engages a larger gear 251 coupled to the drive shaft 36 or drive spool 365, using any number of well known gearing mechanisms. Providing a gear assembly 251, 252 between the drive motor 25 and the drive shaft 36 or drive spool 365 can increase the torque applied to the drive shaft 36, adjust the rotational rate of the transducer array with respect to the motor rotation rate, and/or allow the drive motor 25 to be a reusable part that connects to the gear assembly 251, 252 when the catheter 1 is coupled to the handle 2 just prior to use.

Figure 11D:
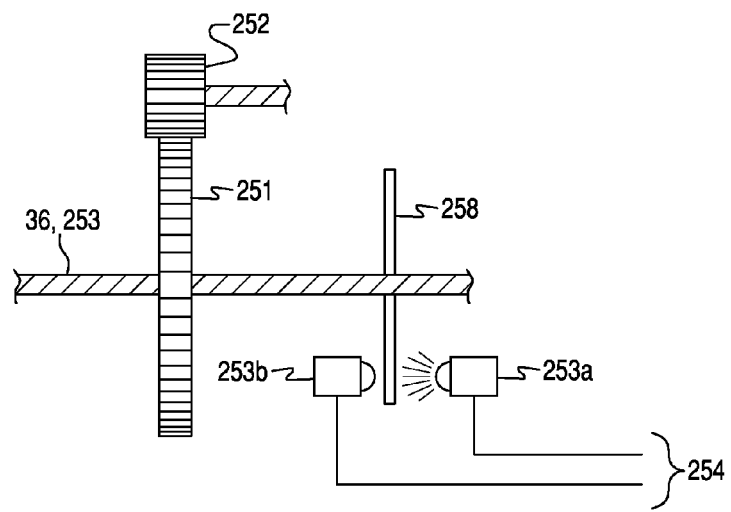
Figure 11E:
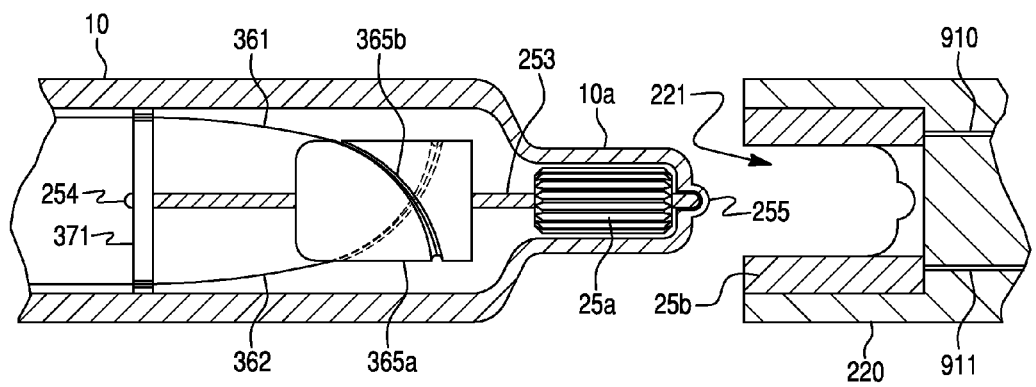

In a further embodiment, the drive assembly may include a rotation sensor to inform the handle controller or system controller of the position of the transducer array. For example, FIG. 11C shows a rotation sensor 256 coupled to the drive motor 25, such as by a gear 255, to record the rotational orientation of the drive shaft 36 or drive spool 365. The rotation sensor 256 may be any of a number of commercially available rotation counters that generates a signal transmitted by a conductor 257 to the handle controller or system controller. FIG. 11C also shows an alternative rotation sensor including an optical sensor 253 configured to sense optical properties on the large drive gear 251 to sense the rotational orientation of the gear. Such an optical sensor 253 may read markings, optical properties, or other indicia on the drive gear 251 and provide a signal via a conductor 254 to the handle controller or system controller which can use information in the signal to determine the gear's rotational orientation, and thereby estimate the transducer's rotational orientation. A third configuration for a rotation sensor is illustrated in FIG. 11D, which includes an optically encoded disc 258 coupled to an axel 253 or drive shaft 36 coupled to the large drive gear 251, and an optical sensor including an illuminator part 253a and light sensor part 253b. The illuminator part 253a and light sensor part 253b are positioned on either side of the optically encoded disc 258, as illustrated, or on the same side of the optically encoded disc 258, so that the light from the illuminator part 253a is transmitted through or reflected off of the optically encoded disc 258 and received by the light sensor part 253b. The optically encoded disc 258 includes optical properties, shapes or patterns that enable a controller to determine the rotational orientation of the disc based upon signals received from the light sensor part 253b. For example, the optically encoded disc 258 may include a circumferential stripe near the outer rim that exhibits a transparency gradient, such as ranging from 100% transparent to 100% opaque, which may be generated using a number of photographic or computer-image generating processes. With such a gradient stripe, a controller receiving a light intensity signal from the light sensor part 253b can calculate the rotational orientation based upon the amount of light transmitted. Alternatively, the illuminator part 253a and light sensor part 253b may be positioned on the same side of the optically encoded disc 258 and the circumferential stripe feature a continuous gradient from 100% transparent to 100% reflective. In both of these alternatives, the controller can calculate the value of received light intensity divided by the intensity of the light source, a fraction that can be correlated to the rotational orientation of the optically encoded disc 258.

In another embodiment of the drive motor 25, the motor's rotor portion 25a may be sealed within a thin walled portion 10a of the catheter body 10 that is configured to slip into a reusable stator portion 25b positioned in the handle. This alternative enables the catheter assembly 1 to be fashioned as a fully sealed unit that slips into a reusable handle 2 which includes a reusable stator portion 25b of the motor 25. This embodiment may include a rotor 25a coupled to a rotor shaft 253 that is rotatably fixed on both ends, such as via a first bearing in a divider plate 371 and a second bearing 255 in the thin walled portion 10a of the catheter body 10. The stator portion 25b may be sealed within a portion of the handle structure 220, with an opening 221 configured to accept the thin walled portion 10a of the catheter assembly. The rotor portion 25a may be coupled to either a drive shaft 36 or a drive spool 365 according to any of the embodiments described herein.

In a further embodiment, the stator of the drive motor 25 may be removable and configured to slip over the rotor of the drive motor 25 when the catheter 1 is coupled to the handle 2 just prior to use. This would allow reusing a portion of the drive motor 25 while providing the catheter assembly 1 as sterile, sealed assembly.

Figure 12A:
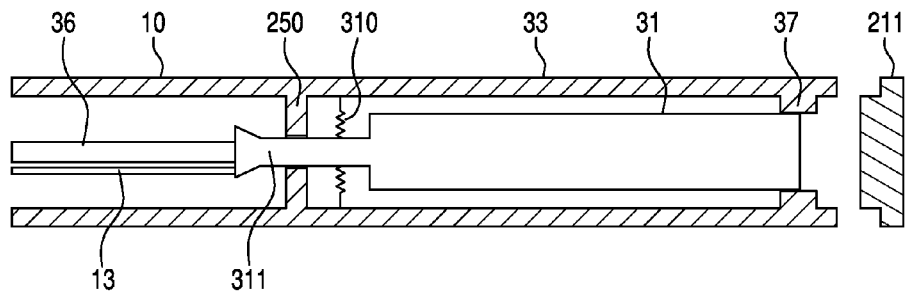
FIGS. 12A-12C are cross sectional views of details of alternative embodiments of the distal end of the dynamic ultrasound imaging catheter.
Figure 12B:
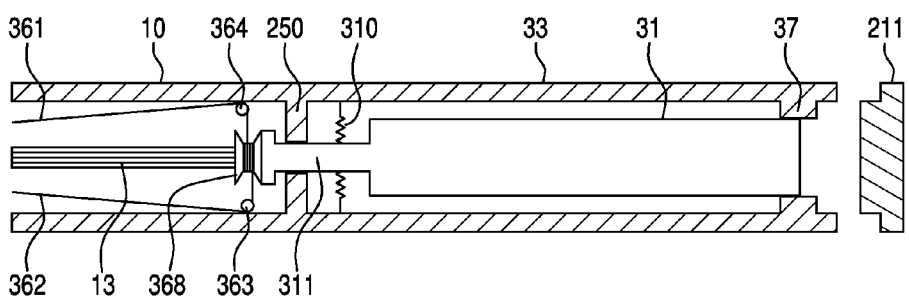
Figure 12C:
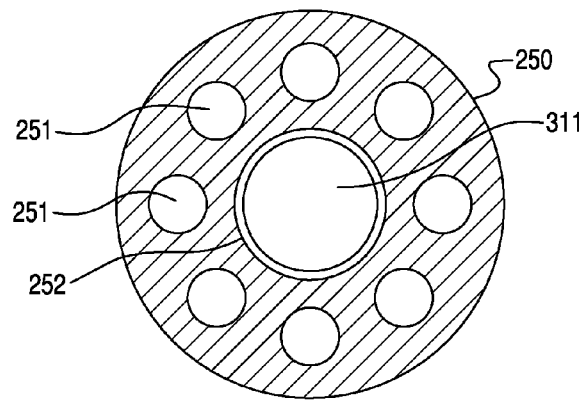

Another embodiment of the distal portion of the catheter assembly 1, which is illustrated in FIGS. 12A-12C, includes a flexible fluid seal 310 coupled between the catheter body 10 and a portion of the transducer array 31. Referring to FIGS. 12A and 12B, the flexible seal 310 may be made of Mylar® or other flexible plastic sheet material with sufficient excess material to allow the transducer array 31 to rotate with respect to the window portion 33. For example, sufficient excess material in the flexible seal 310 may permit the transducer array to turn approximately 45 degrees one direction and 45 degrees in the other direction to provide a total rotation angle of 90 degrees. Since the dynamic ultrasound imaging catheter is a single use device, the flexible seal 310 can be designed to last a limited number of cycles. Using a flexible fluid seal 310 coupled between the catheter body 10 and a portion of the transducer array 31 allows the bearing device at the proximal end of the transducer array to be a simple slip ring 250, saving on the cost and complexity of a fluid boundary bearing as described above. In this embodiment, the transducer array 31 may include an extension shaft 311 aligned with the centerline of the transducer array 31 and extending a distance in the proximal direction to provide an attachment surface for the a flexible fluid seal 310 and a bearing surface for rotationally interfacing with the slip ring 31. The proximal end of the extension shaft 311 can connect to a drive wire 36, as illustrated in FIG. 12A, or to a drive spool 368, as illustrated in FIG. 12B. Also, the wire harness 13 may connect to or through the extension shaft 311. In this embodiment, the transducer array 31 is maintained in the center of the window portion 33 of the catheter by the slip ring 250 encircling the extension shaft 311 on the proximal end and by a distal bearing 37 like that illustrated in FIG. 4E encircling or contacting a distal portion of the transducer array 31. As described herein with respect to other embodiments, the end cap 211 illustrated in FIGS. 12A and 12B may be removable prior to use, or a self sealing cap of any number of known configurations.

Referring to FIG. 12C, the slip ring 250 may be a simple disc with a centerline through-hole 252 sized to be slightly larger than the extension shaft 311. The centerline through-hole 252 may be coated with a low-friction coating, like Teflon®, or the slip ring 250 itself may be made from a low-friction material like Teflon® so that the extension shaft 311 can turn freely. Peripheral through-holes 251 may be provided in the slip ring 250 to permit fluid to flow through it or to allow pressures to equalize on both sides of the slip ring 250 so that the extension shaft 311 is not longitudinally displaced by pressure differences between the proximal and distal ends of the catheter.

In embodiments in which the acoustic coupling fluid is added to the window portion 33 at the time of use, the clinician may remove the end cap 211 and pour or inject the acoustic coupling fluid through the distal bearing 37. For example, the distal bearing 37 illustrated in FIG. 4E includes gaps between the pads 37b through which the acoustic coupling fluid can be introduced. A filling tool may be used, such as a funnel or a syringe, in this process, though care should be taken to avoid introducing bubbles into the window portion. Once the window portion 33 has been filled with acoustic coupling fluid, the end cap 211 can be reattached, such as by pressing on it to form a snap seal.

In an embodiment in which sterile saline solution is flowed through the catheter during operation, the distal portion of the catheter may use the slip ring 250 and distal bearing configuration as illustrated in FIGS. 12A-12C with the exception of the flexible seal 310. In such an embodiment, the end cap 211 is removed prior to injecting saline solution at the time of use.

The through-holes 251 in the slip ring 250 permit saline solution to flow freely into the window portion 33, and gaps in the distal bearing 37 between the bearing pads 37b illustrated in FIG. 4E permit saline solution to exit the tip of the catheter.

Control of the dynamic motion of the transducer array 31 can be accomplished using circuitry similar to that illustrated in FIG. 13. Torque is applied to the drive wire 36 by an electric motor 25 which may be a stepper motor 25 or other electric motor. Power to the motor 25 can be provided by a power control circuit 902 coupled to an electric power source 903 and controlled by a controller 901 by means of leads 910, 911. The power control circuit 902 provides power from power source 903 with polarity and in increments (e.g., pulses or steps) in response to commands received from the controller 901. The power control circuit 902 may be one or more power transistors that are gated on/off by signals received from leads 910, 911. The controller 901 receives control inputs from an operator by buttons 23, 24, for example, which may be simple switches 923, 924 that provide simple on/off signals on inputs to the controller 901. The controller 901 can receive signals from the motor 25 via lead 913 and/or the power control circuit 902 via lead 912 that it can use to determine the position of the transducer array 31, as explained below. The buttons 23, 24 are optional because the controller 901 can receive control inputs from the ultrasound system 150, which may run an autonomous scanning routine and/or receive user inputs via keyboard, mouse, touch-screen or other user interface device. The controller can also provide status and transducer orientation information to the ultrasound system 150 and receive timing and motor control signals from the ultrasound system 150 via input/output leads 915.

The controller 901 may be a microprocessor or microcontroller with internal or external memory positioned within the handle assembly 2, within the isolation box 130 or within the ultrasound system 150. Alternatively, the controller 901 may be incorporated within the operating software of the ultrasound system 150 itself. The power source 903 may be a battery (e.g., one or more disposable batteries) within handle assembly 2 or isolation box 130, or may be a power source (e.g., a DC power supply) within the ultrasound system 150 itself.

In an embodiment, each of the components shown in FIG. 13 can be positioned within the handle assembly 2. In other embodiments, only the buttons 23, 24, motor 25 and power control circuits 902 are positioned in the handle assembly, with the other components and functions positioned or performed in the isolation box 130 or ultrasound system 150. In yet another embodiment, only the motor 25 is positioned within the handle assembly with the other components positioned within a catheter holder assembly (not shown), the isolation box 130 and/or the ultrasound system 150.

In embodiments employing a drive wire 36, software or circuitry based mechanisms may be included to prevent kinking of the drive wire 36. In an embodiment, the drive motor 25 is configured to produce a maximum torque that is less than a critical torque that could cause the drive wire 36 to kink. This may be achieved by limiting the power of the drive motor 25, or by monitoring the power applied to the drive motor 25, such as with the controller 901, and cutting off power to the drive motor 25 before the critical torque level is reached. In a further embodiment, the controller 901 (or the drive motor 25) may be programmed and configured to limit drive motor 25 rotation so that it does not turn the transducer array 31 beyond its rotational limits. Additionally, centering discs 240i positioned periodically along the catheter body 10 will help prevent kinking of the drive wire 36 under torque conditions.

While not specifically shown in FIGS. 3-13, the various embodiments include a temperature sensor, such as a thermistor as illustrated in FIG. 2, positioned near the transducer array 31 so as to sense the temperature of tissues exposed to ultrasound energy. Signals from the temperature sensor are routed to the isolation box 130, and in some embodiments, to the ultrasound system 150 so that ultrasound imaging can be automatically terminated if tissue temperatures approach a dangerous level.

The various embodiments provide a maximum scanning angle through which the transducer array 31 can be rotated. This maximum scanning angle may be 30, 60, 90, 120 or 180 degrees, for example, or any angle in between. The limiting design factor in determining the maximum scanning angle is the maximum twist that can be sustained by the wire harness 13 or other catheter components (e.g., a flexible seal 310). As the transducer array 31 rotates, the distal end of the wire harness 13 rotates with it while the proximal end remains fixed. In embodiments where the wire harness twist extends over most of the length of the catheter 1, such as in embodiments shown in FIGS. 3, 4A, 4B, and 10A-10D, a larger scanning angle (e.g., 90 to 180 degrees) may be implemented without causing the wire harness to tangle or pull out of connections at either end of the catheter. In embodiments where the wire harness twist extends over a limited distance, such as in embodiments shown in FIGS. 6A and 6B, the maximum scanning angle may need to be limited, such as to 60 degrees or less, to avoid tangling or placing the wire harness 13 in tension such that electrical connections are broken. By providing extra length (i.e., slack) in the portion of the wire harness 13 that will experience twisting, the maximum scanning angle can be increased. When implementing a particular embodiment, the maximum scanning angle may be determined based upon physical limitations, such as maximum allowable wire harness twist, and then implemented in the control circuitry and/or software control instructions so that operational scanning angle is less than the maximum physical scanning angle in order to prevent damage to the transducer array 31 and wire harness 13.

Figure 14:
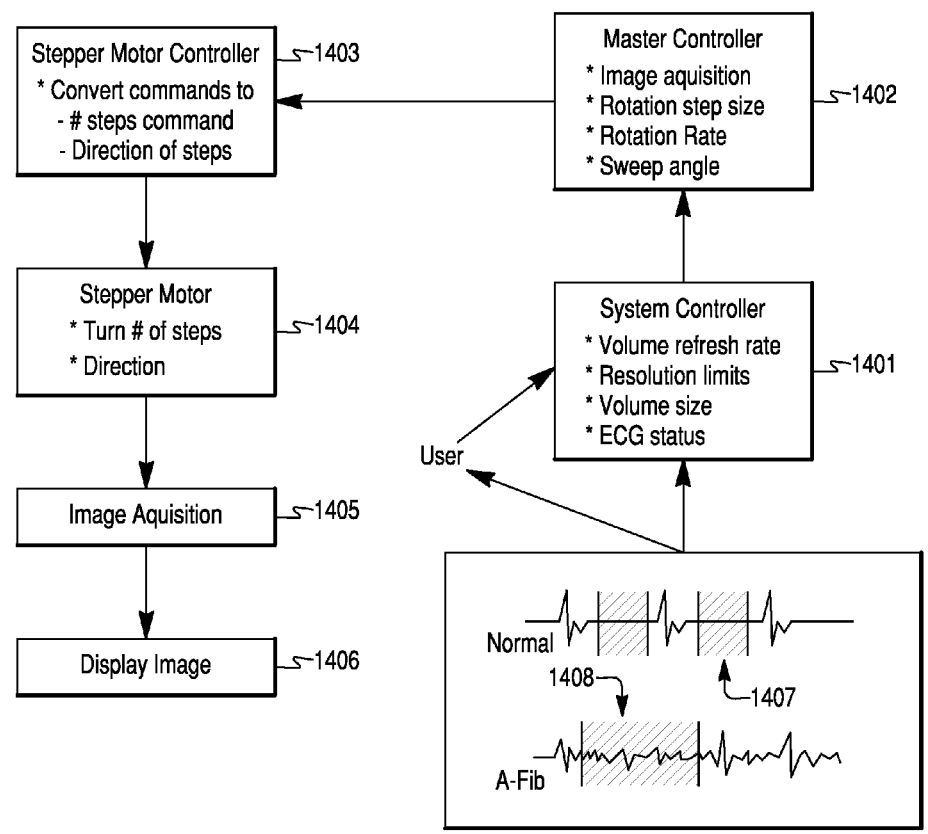
FIG. 14 is a block/flow diagram of a method for controlling the operation of the transducer array according to an embodiment.

A dynamic imaging catheter system according to the various embodiments may be used in conjunction with an ultrasound system as illustrated in FIG. 14. A user may interface with a top level system controller functionality within the ultrasound system (e.g., by means of a mouse and keyboard) to define basic parameters of the ultrasound imaging to be conducted, step 1401. For example, the user may specify the rate at which the volume images are to be refreshed (i.e., re-imaged) and the desire minimum resolution desired. The user may also define the size of the volume to be imaged in terms of scan angle (or frame angle), transducer rotation angle, and imaging depth. As a further input, the user may select a feature in the ECG signal to use as an imaging trigger, set an ECG test condition (e.g., a test to detect atrial fibrillation), or select an imaging program based upon the ECG status.

In selecting these various imaging parameters, the ECG status may be considered by the clinician to determine the appropriate imaging program to employ. For example, in a normal heart indicated by a normal ECG pattern, the heart exhibits periods of relative rest 1407 in which there will be less movement frame-to-frame in a dynamic image scan. Thus, in a normal heart, the appropriate imaging program may consist of a series of full ultrasound frames may be taken at each of a number of rotational orientation steps across the entire rotational range. A healthy heart imaging program may also include obtaining two or more frames per orientation step to obtain more image data and thus enable better image processing. Also, imaging operations may be conducted to exclude the QRS complex, imaging only during the intra-beat periods 1407.

However, in a diseased heart exhibiting atrial fibrillation, for example, the heart may exhibit continuous, high-frequency movements indicated by rapid irregular ECG signals 1408. With the heart quivering unpredictably, heart tissue is likely to move enough to cause image blurring (or blurring of compound images) over the span of a full rotation scan, and even over a full frame scan (i.e., maximum sweep angle). In such conditions, the appropriate imaging program may consist of performing many short duration scans across less than the full sweep angle per frame and less than the entire rotational range. By increasing the frame rate (i.e., number of two-dimensional images per second), clear images of the rapidly moving heart may be obtained. Since frame rate is inversely proportional to viewing angle and inversely proportional to imaging depth, the imaging program may involve reducing the viewing angle and/or the imaging depth. Additionally, the rotation rate of the transducer array may be increased to obtain an image volume that represents very short intervals of time. Alternatively, the rotation step size may be increased so that a complete scan can be obtained in fewer steps. Also, the imaging may be conducted for a longer time, covering much of the atrial fibrillation period 1408, in order to obtain more data for viewing and image processing.

Once the user has selected the appropriate ultrasound imaging parameters, the system controller function may provide these parameters in the form of commands to the master controller function. The master controller then determines when images should be acquired, calculates the necessary rotation step size, rotation rate and sweep angle to obtain ultrasound image consistent with the user supplied parameters, step 1402. The master controller then provides control signals to the stepper motor controller function. The stepper motor controller converts the received control signals into electrical pulses supplied to the stepper motor which determines the direction and number of steps the motor moves through before stopping, step 1403. The stepper motor then turns in response to the electrical pulse provided by the stepper motor controller, step 1404. When the stepper motor stops at a step, the system acquires one or more image frames, step 1405. These image frames are transmitted by the ultrasound imaging catheter as ultrasound signal data to the ultrasound imaging system, which stores the image data and generates a display, step 1406.

Depending upon the displayed imagery, the user may adjust imaging parameters, repeating step 1401, in order to obtain better or different image resolution. Also, if the user observes a change in the ECG pattern, the user may initiate a different imaging program as appropriate.

The ultrasound system may also receive ECG signals directly and, using a pattern recognition algorithm, detect when the heart is in a normal rhythm or in an abnormal state, such as atrial fibrillation, and automatically select the appropriate imaging program to use.

In the foregoing process illustrated in FIG. 14, the system controller function 1401, the master controller 1402 and the steps of acquiring images 1405 and displaying images 1406 may all be accomplished in software operating on one or more system processors (e.g., workstations). In an embodiment, each of these functions may be separate software modules operating on the same workstation processor. In this embodiment, the system processor is adapted and configured by operating software and electronic connections, including connectors for electrically connecting to the ultrasound imaging catheter, to direct the rotation of the transducer array using the stepping motor controller, to direct the acquisition of ultrasound image data, to receive the ultrasound data, generate ultrasound image frames from the ultrasound data, and display the ultrasound images. In another embodiment, the functions may be accomplished in software operating on multiple processors, such as a system processor running system controller and master controller software modules coupled to an ultrasound imaging system workstation operating software to perform the image acquisition 1405 and image display 1406 functions.

Figure 15:
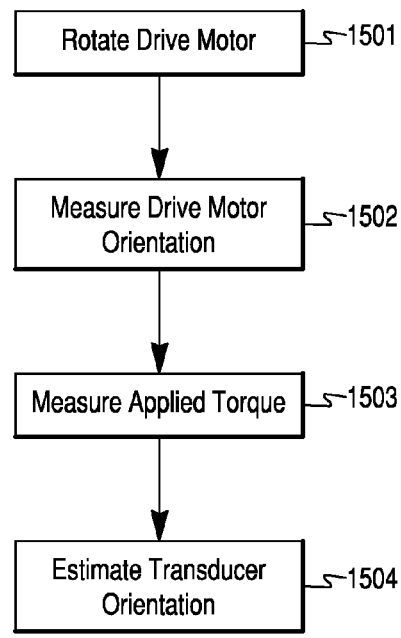
FIG. 15 is a flow diagram of a method for determining the rotational orientation of the transducer array according to an embodiment.

During the imaging process, it is important for the imaging system processor to be able to estimate the rotational orientation of the transducer array at the instant an image frame is obtained. However, the transducer array is at the distal end of the catheter, which makes it difficult to directly measure its orientation. Methods for estimating the transducer orientation are disclosed in U.S. patent application Ser. No. 11/610, 357 entitled "Catheter Position Tracking for Intracardiac Catheters" and Ser. No. 11/610,386 entitled "Catheter Position Tracking Methods Using Fluoroscopy and Rotation Sensors," both filed on Dec. 13, 2006, both of which are incorporated by reference in their entirety. Additionally, the transducer rotational orientation may be estimated by the imaging system processor based upon information obtained by the processor from the stepper motor and an optional rotational orientation sensor 253, 256, as illustrated in FIG. 15. In this method, the after the drive motor has rotated an increment, step 1501, the drive motor orientation is communicated to the system processor, step 1502. The drive motor orientation may be obtained from the stepper motor controller or a separate rotational orientation sensor 253, 256. The rotational position of the stepper motor does not necessarily correspond to the rotational orientation of the transducer array due to twisting of the drive wire 36 or stretching of the drive line 361, 362. To compensate for this, the torque applied to the drive wire 36 or drive spool 365 may be measured and communicated to the system processor, step 1503. Torque may be measured by any number of known mechanisms. Having data both the drive motor orientation and applied torque to hold the present rotational position, the system processor can then estimate the transducer's rotational orientation, step 1504. Assuming constant elasticity of the drive wire 36 or drive line 361, 362 over the range of applied torques, the angular difference between the orientation of the transducer array and the measured rotational position of the drive motor is a constant times the applied torque. Thus, the system processor can estimate transducer rotational orientation by implementing an algorithm that computes the drive motor's measure rotational position plus a correction constant multiplied times the applied torque (which will be positive or negative depending upon the direction in which torque is applied). This correction constant can be estimated based upon the material properties and length of the drive wire 36 or drive line 361, 362, or may be measured during design and development.

In an alternative embodiment, a constant speed motor may be used instead of a stepper motor, with ultrasound image frames obtained periodically throughout the rotational scan. By measuring the drive motor's orientation at the time each ultrasound image is obtained, the system processor can estimate the orientation of the transducer array at the time of the image using methods similar to that illustrated in FIG. 15. When ultrasound image frames are obtained while the transducer array is rotating, the resulting images will be inclined with respect to the direction of rotation in an amount proportional to the rotation rate (i.e., degrees per unit time). This small imaging error may be acceptable and may be processed out by the imaging system processor. Such a system may exhibit nonlinear transducer-to-drive motor rotational differences toward the maximum rotational angles as the drive motor stops and reverses direction and the transducer array follows suit. To avoid increased imaging errors, and simplify the transducer orientation estimating procedure, the system processor can be programmed to simply not image or ignore images obtained near the rotation angle limits, taking/storing images in the center of the rotation sweep where the transducer orientation is more predictable.

In embodiments using drive lines 361, 362, additional compensation may be required to account for differences in the drive line lengths caused by bending of the catheter body. For example, a ninety-degree bend over a one inch radius of a nine French catheter results in a difference of 4 millimeters between opposite sides of the interior of the catheter. Thus, if the drive lines are on opposite sides of the catheter, bending of the catheter will cause the transducer array to turn slightly. This effect can be reduced by passing the drive lines 361, 362 side by side in the catheter. A correction factor can be determined by the system processor based upon measuring the steering controller position and applying a correction factor based upon the measured position.

Using the foregoing methods, the system processor can thus estimate the rotational orientation of the phased array transducer with respect to its imaging centerline or the window portion 33 of the catheter at each instant, and particularly when each ultrasound image frame is obtained. In operation, the system processor can control the processes of rotating the phased array transducer (via commands to the step motor controller) and generating ultrasound images (via commands to the beam former circuits) so that ultrasound images are obtained when the transducer array is stopped at a particular rotational orientation (versus during movement). Also, the system processor can record the estimated rotational orientation of the transducer with each generated ultrasound image frame, so each image is correlated to the transducer rotational orientation at the time the image was obtained. By correlating image frames with the transducer orientation at the time each image was obtained, the system processor generates and stores information that can be used to construct three-dimensional images by merging, combining or otherwise processing the data. As with other functions performed by the system processor, the processor is adapted and configured to perform the functions via software operating in the processor. Additionally, the processor can be configured with electrical connections (e.g., standard input/output ports and data cables) for transmitting commands to the stepper motor controller (or other type of motor controller) and the ultrasound beam former circuits, and receiving signals from the stepper motor controller (e.g., related to motor orientation and applied torque) and ultrasound data signals from the beam former circuits.

The various embodiments of the ultrasound imaging catheter may be assembled using methods similar to those used to assemble conventional ultrasound imaging catheters, with the additional consideration that the rotational elements of the ultrasound imaging assembly 3 need to be physically aligned and seated within the catheter body 10. The distal portion of the catheter body 10, including the acoustic window portion 33, may be fabricated as separate parts that are joined to the catheter body 10 during assembly of the catheter system 1. This option may facilitate assembly because any seating or limiting structures (e.g., bearing seat 350 and lip 350A) that mate or contact rotating elements of the ultrasound imaging assembly 3 can be provided in a relatively short separate part while the majority of the catheter body 10 comprises a smooth bore elongated tube. In this configuration, the internal elements of the catheter system 1 can be fed through the main catheter body tube, and followed by seating and aligning of the moving parts to a short distal segment of the catheter which is then glued or otherwise bonded to the main catheter body tube. Further, there may be multiple short distal sections, such as a bearing seating portion and an acoustic window portion 33, which are sequentially assembled over the internal elements and bonded to the rest of the catheter. Short sections may also be used to facilitate positioning centering discs 240*i* and passing the drive wire 36 and wire harness 13 through the discs. (This embodiment of multiple distal catheter segments is presumed in the assembly flow process illustrated in FIG. 16 for example purposes only.) For the embodiments in which the acoustic coupling fluid is added at the time of manufacture, once all components are assembled and proper rotational operations confirmed, acoustic coupling fluid can be added to the fluid filled gap 32 and the distal cap 211 can be glued or otherwise bonded to the open end of the short distal segment of the catheter. For the embodiments in which the clinician adds acoustic coupling fluid at the time of use or sterile saline is flowed through the catheter during use, a shipping/storage cap can be applied after proper rotation operations are confirmed.

Figure 16:
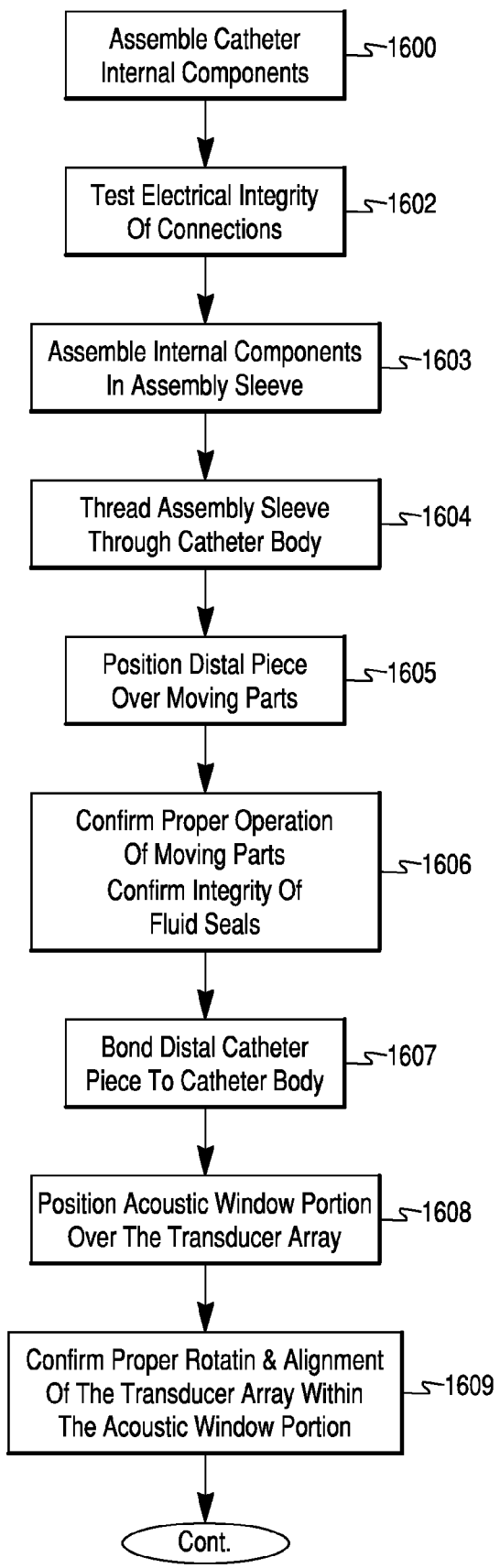
FIG. 16 is a flow diagram of a method for assembling an embodiment of the dynamic ultrasound imaging catheter.
Figure 16:
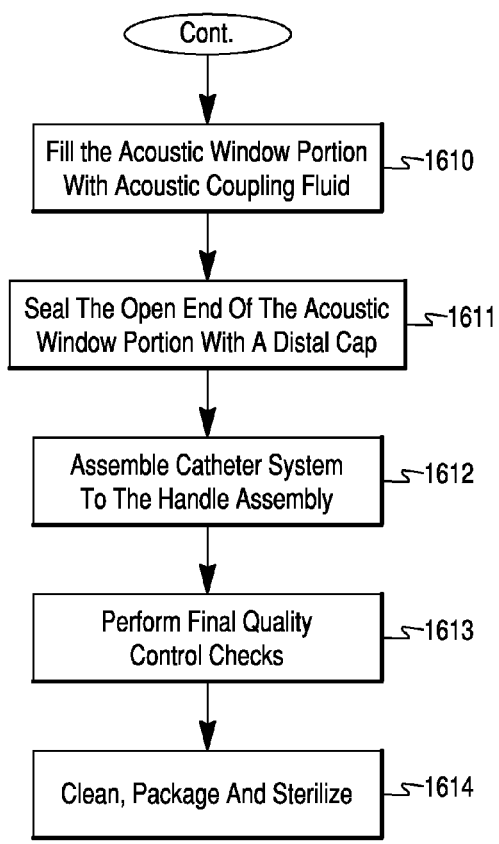

Referring to FIG. 16, the various internal elements of the catheter (i.e., those parts that fit within the catheter body 10) are first assembled, step 1601, and quality checked to ensure all electrical and mechanical connections are properly made, step 1602. The wire harness 13 and steering wires 11, 12 may be connected to the handle assembly 2 at this time or later (e.g., after assembly of the catheter 1), step 1612. The internal elements are then fitted into an assembly sleeve or other assembly jig, step 1603, and threaded into the main catheter body and the assembly sleeve removed, step 1604. In embodiments using separate distal catheter portions, the moving parts of the ultrasound imaging assembly 3 will now be extending from the distal end of the main catheter body. Next, the distal portion of the catheter containing seating, positioning and sealing structures (such as bearing seats and grooves) is fitted over the ultrasound imaging assembly 3 so that seating surfaces are properly aligned and mated to the corresponding structures (e.g., bearings 35, 365 and a divider disc 240, depending upon the particular embodiment), step 1605. At this point, the proper rotational operation of the ultrasound imaging assembly 3 moving parts may be confirmed, and alignments adjusted as necessary, step 1606.

Once proper alignment and rotational operation are confirmed, the distal portion of the catheter can be bonded to main catheter body, step 1 607. It is worth noting that the steps of bonding catheter segments together can be performed later after all parts have been assembled. Next, the acoustic window portion 33 can be positioned over the transducer array 31, step 1608, and the alignment checked to confirm the array does not contact the interior surface of the window portion during rotation, step 1609. This step may involve engaging a bearing seat 350 with the proximal bearing 35 if the bearing seat is provided in the window portion. If a distal bearing 37 is used in the implemented embodiment, this bearing can be positioned on the transducer array 31 as part of this step.

Once proper alignment of the acoustic window portion 33 and the transducer array 31 and rotational operation are confirmed, the acoustic coupling fluid can be added and all bubbles removed, step 1610. Next, the distal end of the catheter can be sealed by positioning the distal cap 211 over the opening and bonding it to the acoustic window portion 33, step 1611. Depending upon the design, this step may involve aligning and seating the distal bearing 37 on a bearing seat provided in the distal cap 211. The catheter assembly may then be connected to the handle assembly, connecting the wire harness 13 to a cable 21 and steering wires 11, 12 and/or drive wires 361, 362 to the drive mechanisms in the handle (e.g., the deflection manipulator 22 and/or drive motor 25), step 1612.

Now fully assembled, the catheter assembly can be given final quality control and functional checks, step 1613, and then cleaned, packaged and sterilized, step 1614. As noted above, the presence of the acoustic coupling fluid in the catheter in some embodiments may dictate the use of particular sterilizing methods, such as chemical cleaning prior to packaging followed by gamma radiation exposure within the sealed packaging.

The foregoing steps may be performed in any order, and the illustrated and described order is but one possible sequence for assembling various embodiments. For example, the steps of positioning the acoustic window portion 33 and distal catheter portion over the moving parts of the ultrasound imaging assembly 3, one or more of steps 1605-1611, may be performed and quality confirmed before the rest of the catheter internals are threaded into the main catheter body, step 1604.

Once assembled, tested and sterilized, the dynamic ultrasound imaging catheter assembly can be packaged in a sterile package, such as a plastic bag that is thermally sealed on all edges to maintain the sterility of the catheter assembly, to form a medical diagnostic kit. This kit may further include a cable with connectors for electrically connecting the ultrasound imaging catheter assembly to a system processor, a supply of acoustic coupling fluid to be inserted into the window portion, one or more filling tools to aid in filling the window portion with acoustic coupling fluid, and instructions explaining the preparation and use of the catheter.

Typical operation of the various embodiments of a dynamic ultrasound imaging catheter is illustrated in FIG. 17. As with conventional ultrasound imaging catheters, the imaging portion (i.e., the distal portion containing the ultrasound imaging assembly 3) of the catheter is inserted into the subject via standard catheterization procedures, step 1701. As part of this step, the catheter may be advanced with the tip portion deflected in order to thread the catheter into the veins or ventricles of the heart. The location of the transducer array may then be determined, step 1702, using known procedures, such as fluoroscopy, and/or recently invented methods and devices disclosed in U.S. patent application Ser. No. 11/610, 357 entitled "Catheter Position Tracking for Intracardiac Catheters" and Ser. No. 11/610,386 entitled "Catheter Position Tracking Methods Using Fluoroscopy and Rotation Sensors," previously incorporated by reference. As explained in those patent applications, determining the location and orientation of the transducer array is important to be able to assemble a series of ultrasound images into a composite, such as a composite three-dimensional image. With the catheter positioned in the patient's organ (e.g., the heart), the clinician may obtain and view ultrasound images to confirm that the catheter is properly positioned to image the portion of the organ desired, step 1703. In this step, the clinician may view the live ultrasound image to see what part of the organ is imaged. If the clinician determines that the transducer is in an incorrect position or orientation, the steps 1701-1703 of position and confirming the location of the catheter and viewing live images may be repeated until the desired viewing perspective is achieve. Next, the clinician may scan the transducer array through its viewing angle (i.e., rotation angle) while viewing the live ultrasound image to confirm that the image volume encompasses the portion of the organ to be imaged, step 1704. The clinician may do this by pressing a button 23, 24 on the handle assembly 2 while viewing the ultrasound system display. By pressing one or both buttons, or selecting a menu option on the ultrasound control system, the clinician can direct the system to rotate the transducer array a single angular increment at a time or continually scan back and forth through the scanning angle. If the clinician is dissatisfied with the imaging volume, he or she may rotate the catheter assembly by twisting the handle, thereby adjusting the rotational orientation of the catheter (and thus the orientation of the imaging volume), and then repeat steps 1703 and 1704 of confirming that the imaging volume encompasses the desired volume of the organ being imaged.

Once the clinician has confirmed proper position of the transducer array to image the desired volume, the clinician can then begin ultrasound imaging while scanning (oscillating) the transducer array back and forth through the scanning angle by pressing one or two buttons 23, 24 on the handle assembly 2, step 1705. In this step, the ultrasound system automatically rotates the transducer array back and forth through the scanning angle while obtaining and storing ultrasound images. Ultrasound images are stored in memory within the ultrasound system along with data indicating the transducer array angle of rotation and time of each image. Once sufficient images have been obtained, the clinician may reposition the catheter to image a different volume of the patient in step 1707 by more or less repeating steps 1701-1706. The imaging session is terminated in the same manner as conventional catheterization procedures. Finally, the stored images can be reviewed, processed and combined using the ultrasound system or other image processing systems, step 1708. This processing may include stitching together a series of images to produce composite three-dimensional images.

By automatically rotating the transducer array, the ultrasound catheter can generate the image data necessary to create three-dimensional composite images without requiring the clinician to rotate the catheter or otherwise manage the scanning motion. By repeatedly and accurately rotating the catheter through the scanning angle, many images can be obtained across the angle of rotation without increasing the workload of the clinician.

The various embodiments provide an imaging ultrasound transducer array assembly that can scan through a range of viewing angles, such as 30, 60 or 90 degrees about the longitudinal axis. The transducer array provides a planar image spanning typically about 90 degrees parallel to the longitudinal. Thus, the various embodiments can provide ultrasound image data encompassing a volume spanning about 90 degrees parallel to the transducer array long axis and about 30, 60 or 90 degrees perpendicular to the transducer array long axis. Additionally, by noting the transducer rotational orientation and time associated with each planar image, the ultrasound imaging data can be saved in the ultrasound system for subsequent processing into three-dimensional and four-dimensional (including time) composite images encompassing the imaged volume.

There are several benefits to providing a controlled axial oscillating rotation capability. For instance, the present invention will enable generation of three-dimensional axial views of tissue even when the tip of the catheter is in a deflected (i.e., bent) configuration. This is achievable because the transducer array turns within the catheter, instead of rotating the whole catheter body.

The various embodiments also simplify some of the tasks that a physician must perform during imaging procedures. The instant invention allows the physician to smoothly rotate the imaging transducer array within a catheter by simply pressing a button on the handle assembly or activating a control on the ultrasound system, thereby obviating the need to rotate the handle by twisting the wrist or arm to turn the catheter along its axis. By controlling the transducer array rotation/orientation using the stepper motor, the potential for injury to the patient from movement of the catheter body is eliminated.

While the present invention has been disclosed with reference to certain exemplary embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

I claim:

1. An ultrasound imaging catheter, comprising:
   a catheter body having proximal and distal ends and a diameter limited in size to less than about 10 French (3.3 mm);
   an acoustic window portion coupled to the distal end of the catheter body, the acoustic window portion having an interior surface;
   a phased array ultrasound transducer housed within the acoustic window portion, the phased array transducer comprising a long axis and configured so that a gap exists between the phased array ultrasound transducer and the interior surface of the acoustic window;
   an acoustic coupling fluid filling the gap between the transducer array and the interior surface of the acoustic window; and
   a rotor portion of an electric drive motor positioned within a sealed thin walled portion of the proximal end of the catheter body and mechanically configured and coupled to the phased array ultrasound transducer so as to rotate the phased array ultrasound transducer about a long axis of the distal end of the catheter body, wherein the sealed thin walled portion of the proximal end of the catheter body is configured to removably slip into an opening of a separate reusable structure, wherein the opening is configured within a reusable stator portion of the electric drive motor positioned within the reusable structure.

2. The ultrasound imaging catheter of claim 1, further comprising a drive wire mechanically coupling the rotor portion of the electric drive motor to the phased array ultrasound transducer, wherein the drive wire is configured to transmit torque from the drive motor to the phased array ultrasound transducer.

3. The ultrasound imaging catheter of claim 1, further comprising:
   a first drive spool coupled to the rotor portion of the electric drive motor;
   a second drive spool coupled to the phased array ultrasound transducer; and
   two tension lines coupled to the first and second drive spools, wherein the first and second drive spools and two tension lines are configured to transmit a rotational force from the drive motor to the phased array ultrasound transducer for rotating the phased array ultrasound transducer about the long axis of the distal end of the catheter body.

4. The ultrasound imaging catheter of claim 1, further comprising a removable cap coupled to a distal end of the acoustic window portion, wherein the ultrasound imaging catheter is configured so the acoustic coupling fluid can be added to fill the gap between the phased array ultrasound transducer and the interior surface of the acoustic window at the time of use.

5. The ultrasound imaging catheter of claim 1, further comprising:
a removable cap coupled to a distal end of the acoustic window portion; and
a saline injection port coupled to the proximal end of the catheter body, wherein the ultrasound imaging catheter is configured so a stream of acoustic coupling fluid can be injected via the saline injection port and exit via the distal end of the acoustic window portion during use, thereby filling the gap between the phased array ultrasound transducer and the interior surface of the acoustic window when in use.

6. The ultrasound imaging catheter of claim 1, further comprising a first bearing located near a proximal end of the acoustic window portion and coupled between the catheter body and a proximal end of the phased array ultrasound transducer.

7. The ultrasound imaging catheter of claim 6, further comprising a second bearing located near a distal end of the acoustic window portion and coupled between the inner surface of the acoustic window portion and a distal end of the phased array ultrasound transducer.

8. The ultrasound imaging catheter of claim 1, further comprising a flexible fluid seal coupled between the inside surface of the acoustic window portion and the phased array ultrasound transducer.

9. The ultrasound imaging catheter of claim 2, further comprising a plurality of centering discs positioned within and along a length of the catheter body.

10. The ultrasound imaging catheter of claim 1, further comprising a gear coupled between the rotor portion of the electric drive motor and the phased array ultrasound transducer.

11. The ultrasound imaging catheter of claim 10, further comprising a rotation sensor configured to sense a rotational orientation of the drive motor and provide a signal to a system processor indicative of the rotational orientation of the drive motor.

12. The ultrasound imaging catheter of claim 3, wherein at least one of the first and second drive spools comprises two spiral grooves in its exterior with one of the two tension lines winding into one of the two spiral grooves and the other of the two tension lines winding into the other of the two spiral grooves.

13. An ultrasound catheter imaging system, comprising:
a processor;
a reusable structure comprising a reusable stator portion of an electric drive motor; and
an ultrasound imaging catheter configured to be electrically coupled to the processor through the reusable structure, the ultrasound imaging catheter comprising:
a catheter body having proximal and distal ends and a diameter limited in size to less than about 10 French (3.3 mm);
an acoustic window portion coupled to the distal end of the catheter body, the acoustic window portion having an interior surface;
a phased array ultrasound transducer housed within the acoustic window portion, the phased array transducer comprising a long axis and configured so that a gap exists between the phased array ultrasound transducer and the interior surface of the acoustic window;
an acoustic coupling fluid filling the gap between the transducer array and the interior surface of the acoustic window; and
a rotor portion of the electric drive motor mechanically positioned within a sealed thin walled portion of the proximal end of the catheter body and configured and coupled to the phased array ultrasound transducer so as to rotate the phased array ultrasound transducer about its long axis, wherein the sealed thin walled portion of the proximal end of the catheter body is configured to removably slip into an opening of the reusable structure, wherein the opening is configured within the reusable stator portion of the electric drive motor positioned within the reusable structure, wherein the processor is adapted and configured to:
determine a rotational orientation of the phased array ultrasound transducer at a time when ultrasound data is generated by the phased array ultrasound transducer;
receive the ultrasound data from the phased array ultrasound transducer;
generate an ultrasound image using the received ultrasound data; and
correlate the generated ultrasound image with the determined rotational orientation of the phased array ultrasound transducer at the time when the ultrasound data was received from the phased array ultrasound transducer.

14. The ultrasound catheter imaging system of claim 13, further comprising a drive wire mechanically coupling the rotor portion of the electric drive motor to the phased array ultrasound transducer, wherein the drive wire is configured to transmit rotational force from the electric drive motor to the phased array ultrasound transducer for rotating the phased array ultrasound transducer about a long axis of the distal end of the catheter body.

15. An ultrasound catheter imaging system comprising:
a processor; and
an ultrasound imaging catheter configured to be electrically coupled to the processor, the ultrasound imaging catheter comprising:
a catheter body having proximal and distal ends;
an acoustic window portion coupled to the distal end of the catheter body, the acoustic window portion having an interior surface;
a phased array ultrasound transducer housed within the acoustic window portion and configured so that a gap exists between the phased array ultrasound transducer and the interior surface of the acoustic window;
an acoustic coupling fluid filling the gap between the transducer array and the interior surface of the acoustic window;
a drive motor mechanically positioned near the proximal end of the catheter body;
a first drive spool coupled to the drive motor;
a second drive spool coupled to the phased array ultrasound transducer; and
two tension lines coupled to the first and second drive spools, wherein the first and second drive spools and two tension lines are configured to transmit a rotational force from the drive motor to the phased array ultrasound transducer for rotating the phased array ultrasound transducer about a long axis of the distal end of the catheter body, wherein the processor is adapted and configured to:

determine a rotational orientation of the phased array ultrasound transducer at a time when ultrasound data is generated by the phased array ultrasound transducer;

receive the ultrasound data from the phased array ultrasound transducer;

generate an ultrasound image using the received ultrasound data; and correlate the generated ultrasound image with the determined rotational orientation of the phased array ultrasound transducer at the time when the ultrasound data was received from the phased array ultrasound transducer.

16. The ultrasound catheter imaging system of claim 13, wherein the processor is further adapted and configured to control the drive motor.

17. The ultrasound catheter imaging system of claim 13, wherein the processor is positioned within ultrasound system equipment.

18. A medical diagnostic kit comprising:
a sterile package; and
an ultrasound imaging catheter contained within the sterile package, the ultrasound imaging catheter comprising:
   a catheter body having a longitudinal axis, proximal and distal ends, and a diameter limited in size to less than about 10 French (3.3 mm);
   an acoustic window portion coupled to the distal end of the catheter body, the acoustic window portion having an interior surface;
   a phased array ultrasound transducer housed within the acoustic window portion, the phased array transducer comprising a long axis and configured so that a gap exists between the phased array ultrasound transducer and the interior surface of the acoustic window; and
   a rotor portion of an electric drive motor positioned within a sealed thin walled portion of the proximal end of the catheter body and mechanically configured and coupled to the phased array ultrasound transducer so as to rotate the phased array ultrasound transducer about its long axis, wherein the sealed thin walled portion of the proximal end of the catheter body is configured to removably slip into an opening of a separate reusable structure, wherein the opening is configured within a reusable stator portion of the electric drive motor positioned within the reusable structure.

19. The medical diagnostic kit according to claim 18, further comprising a supply of an acoustic coupling fluid for filling the gap between the transducer array and the interior surface of the acoustic window.

20. The medical diagnostic kit according to claim 18, further comprising a filling tool to assist in filling the gap between the transducer array and the interior surface of the acoustic window with an acoustic coupling fluid.

21. An ultrasound imaging catheter, comprising:
a catheter body having proximal and distal ends and a diameter limited in size to less than about 10 French (3.3 mm);
an acoustic window portion coupled to the distal end of the catheter body, the acoustic window portion having an interior surface;
a phased array ultrasound transducer housed within the acoustic window portion comprising a long axis and configured so that a gap exists between the phased array ultrasound transducer and the interior surface of the acoustic window;
an acoustic coupling fluid filling the gap between the transducer array and the interior surface of the acoustic window;
a drive motor positioned near the proximal end of the catheter body;
a first drive spool coupled to the drive motor;
a second drive spool coupled to the phased array ultrasound transducer; and
two tension lines coupled to the first and second drive spools, wherein the first and second drive spools and two tension lines are configured to transmit a rotational force from the drive motor to the phased array ultrasound transducer for rotating the phased array ultrasound transducer about a long axis of the distal end of the catheter body.

22. The ultrasound imaging catheter of claim 21, further comprising a removable cap coupled to a distal end of the acoustic window portion, wherein the ultrasound imaging catheter is configured so the acoustic coupling fluid can be added to fill the gap between the phased array ultrasound transducer and the interior surface of the acoustic window at the time of use.

23. The ultrasound imaging catheter of claim 21, further comprising:
a removable cap coupled to a distal end of the acoustic window portion; and
a saline injection port coupled to the proximal end of the catheter body, wherein the ultrasound imaging catheter is configured so a stream of acoustic coupling fluid can be injected via the saline injection port and exit via the distal end of the acoustic window portion during use, thereby filling the gap between the phased array ultrasound transducer and the interior surface of the acoustic window when in use.

24. The ultrasound imaging catheter of claim 21, further comprising a first bearing located near a proximal end of the acoustic window portion and coupled between the catheter body and a proximal end of the phased array ultrasound transducer.

25. The ultrasound imaging catheter of claim 24, further comprising a second bearing located near a distal end of the acoustic window portion and coupled between the inner surface of the acoustic window portion and a distal end of the phased array ultrasound transducer.

26. The ultrasound imaging catheter of claim 21, further comprising a flexible fluid seal coupled between the inside surface of the acoustic window portion and the phased array ultrasound transducer.

27. The ultrasound imaging catheter of claim 22, further comprising a plurality of centering discs positioned within and along a length of the catheter body.

28. The ultrasound imaging catheter of claim 21, further comprising a gear coupled between the drive motor and the phased array ultrasound transducer.

29. The ultrasound imaging catheter of claim 28, further comprising a rotation sensor configured to sense a rotational orientation of the drive motor and provide a signal to a system processor indicative of the rotational orientation of the drive motor.

30. The ultrasound imaging catheter of claim 21, wherein at least one of the first and second drive spools comprises two spiral grooves in its exterior with one of the two tension lines winding into one of the two spiral grooves and the other of the two tension lines winding into the other of the two spiral grooves.

* * * * *